US008835144B2

(12) United States Patent
Jiang et al.

(10) Patent No.: US 8,835,144 B2
(45) Date of Patent: *Sep. 16, 2014

(54) DUAL-FUNCTIONAL NONFOULING SURFACES COMPRISING TARGET BINDING PARTNER COVALENTLY COUPLED TO POLYMER ATTACHED TO SUBSTRATE

(75) Inventors: Shaoyi Jiang, Redmond, WA (US); Zheng Zhang, Cambridge, MA (US); Shengfu Chen, Hangzhou (CN); Hana Vaisocherova, Prague (CZ)

(73) Assignee: University of Washington, Seattle, WA (US)

( * ) Notice: Subject to any disclaimer, the term of this patent is extended or adjusted under 35 U.S.C. 154(b) by 1267 days.

This patent is subject to a terminal disclaimer.

(21) Appl. No.: 12/493,649

(22) Filed: Jun. 29, 2009

(65) Prior Publication Data

US 2010/0099160 A1  Apr. 22, 2010

Related U.S. Application Data

(63) Continuation of application No. PCT/US2007/089236, filed on Dec. 31, 2007.

(60) Provisional application No. 60/882,821, filed on Dec. 29, 2006.

(51) Int. Cl.
| | |
|---|---|
| *C12N 11/08* | (2006.01) |
| *C12N 11/06* | (2006.01) |
| *C12Q 1/00* | (2006.01) |
| *C12Q 1/68* | (2006.01) |
| *G01N 33/53* | (2006.01) |
| *G01N 33/573* | (2006.01) |
| *G01N 33/545* | (2006.01) |
| *A61K 38/00* | (2006.01) |
| *C07K 17/06* | (2006.01) |
| *C07K 17/08* | (2006.01) |
| *C12N 5/07* | (2010.01) |
| *G01N 33/543* | (2006.01) |

(52) U.S. Cl.
CPC ........ *G01N 33/54353* (2013.01); *G01N 33/545* (2013.01)
USPC ................ 435/180; 435/181; 435/4; 435/6.1; 435/7.1; 435/7.4; 435/29; 435/325; 435/396; 435/397; 436/531; 514/1.1; 530/402

(58) Field of Classification Search
None
See application file for complete search history.

(56) References Cited

U.S. PATENT DOCUMENTS

| | | | |
|---|---|---|---|
| 3,671,502 A | 6/1972 | Samour | |
| 4,075,183 A | 2/1978 | Kawakami | |
| 4,138,446 A | 2/1979 | Kawakami | |
| 4,415,388 A | 11/1983 | Korpman | |
| 4,493,926 A | 1/1985 | Williams, Jr. | |
| 4,985,023 A | 1/1991 | Blank | |
| 5,204,060 A | 4/1993 | Allenmark | |
| 5,714,360 A | 2/1998 | Swan | |
| 5,919,523 A | 7/1999 | Sundberg | |
| 6,361,768 B1 | 3/2002 | Galleguillos | |
| 6,486,333 B1 | 11/2002 | Murayama | |
| 6,897,263 B2 | 5/2005 | Hell | |
| 7,291,427 B2 | 11/2007 | Kawamura | |
| 7,306,625 B1 | 12/2007 | Stratford | |
| 7,335,248 B2 | 2/2008 | Abou-Nemeh | |
| 7,737,224 B2 | 6/2010 | Willis | |
| 7,815,922 B2 * | 10/2010 | Chaney et al. | ................. 424/400 |
| 7,879,444 B2 * | 2/2011 | Jiang et al. | ................. 428/411.1 |
| 2005/0058689 A1 | 3/2005 | McDaniel | |
| 2006/0240072 A1 | 10/2006 | Chudzik | |
| 2007/0042198 A1 | 2/2007 | Schonemyr | |

FOREIGN PATENT DOCUMENTS

| | | |
|---|---|---|
| DE | 10 2006 004 111 A1 | 8/2007 |
| EP | 0 354 984 A2 | 2/1990 |
| EP | 0 419 654 A1 | 4/1991 |
| EP | 0 479 245 A2 | 4/1992 |
| JP | 63-234007 A | 9/1988 |
| SU | 1780673 A1 | 12/1992 |
| WO | 00/39176 A1 | 7/2000 |
| WO | 2004/058837 A2 | 7/2004 |
| WO | 2004/100666 A1 | 11/2004 |
| WO | 2007/068744 A1 | 6/2007 |
| WO | 2007/099239 A2 | 9/2007 |

OTHER PUBLICATIONS

Chang, Y., et al., "Highly Protein-Resistant Coatings From Well-Defined Diblock Copolymers Containing Sulfobetaines," Langmuir 22(5):2222-2226, Feb. 2006.
Chen, S., et al., "Controlling Antibody Orientation on Charged Self-Assembled Monolayers," Langmuir 19(7):2859-2864, Apr. 2003.
Chen, S., et al., "Strong Resistance of Oligo(phosphorylcholine) Self-Assembled Monolayers to Protein Adsorption," Langmuir 22(6):2418-2421, Mar. 2006.

(Continued)

*Primary Examiner* — David M Naff
(74) *Attorney, Agent, or Firm* — Christensen O'Connor Johnson Kindness PLLC

(57) ABSTRACT

Dual-functional nonfouling surfaces and materials, methods for making dual-functional nonfouling surfaces and materials, and devices that include dual-functional nonfouling surfaces and materials. The dual-functional surfaces are nonfouling surfaces that resist non-specific protein adsorption and cell adhesion. The dual-functional surfaces and materials include covalently coupled biomolecules (e.g., target binding partners) that impart specific biological activity thereto. The surfaces and materials are useful in medical diagnostics, biomaterials and bioprocessing, tissue engineering, and drug delivery.

21 Claims, 15 Drawing Sheets

(56) References Cited

OTHER PUBLICATIONS

Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.

Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.

Feng., W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12)2931-2942, Jun. 2004.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.

Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.

Li, L., et al., "Protein Adsorption on Alkanethiolate Self-Assembled Monolayers: Nanoscale Surface Structural and Chemical Effects," Langmuir 19(7):2974-2982, Apr. 2003.

Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.

Lowe, A.B., et al., "Well-Defined Sulfobetaine-Based Statistical Copolymers as Potential Antibioadherent Coatings," Journal of Biomedical Materials Research 52(1):88-94, Jul. 2000.

West, S.L., et al., "The Biocompatibility of Crosslinkable Copolymer Coatings Containing Sulfobetaines and Phosphobetaines," Biomaterials 25:1195-1204, Apr. 2004.

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, J., "Platelet Adhesion Onto Segmented Polyurethane Surfaces Modified by Carboxybetaine," Journal of Biomaterial Science, Polymer Edition 14(12):1339-1349, Dec. 2003.

Yuan, Y., et al., "Grafting Sulfobetaine Monomer Onto Silicone Surface to Improve Haemocompatability," Polymer International 53 (1):121-126, Jan. 2004.

Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.

Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.

Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.

Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zhang, Z., et al., "Superflow Fouling Sulfobetaine and Carboxybetaine Polymers on Glass Slides," Langmuir 22(24):10072-10077, Nov. 2006.

Zhang, Z., "Surface Grafted Sulfobetaine Polymers Via Atom Transfer Radical Polymerization as Superlow Fouling Coatings," Journal of Physical Chemistry B 110(22)10799-10804, Jun. 2006.

Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.

Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.

Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.

"Betaine," Wikipedia, The Free Encyclopedia, <http://en.wikipedia.org/wiki/Betaine> [retrieved Jul. 31, 2011], 1 page.

"Bromide," Wikipedia, The Free Encyclopedia, <http://en.wikipedia.org/wiki/Bromide> [retrieved Jul. 27, 2011], 3 pages.

"Nail Infections," Health911, <http://www.health911.com/nail-infections> [retrieved Aug. 29, 2011], 3 pages.

* cited by examiner

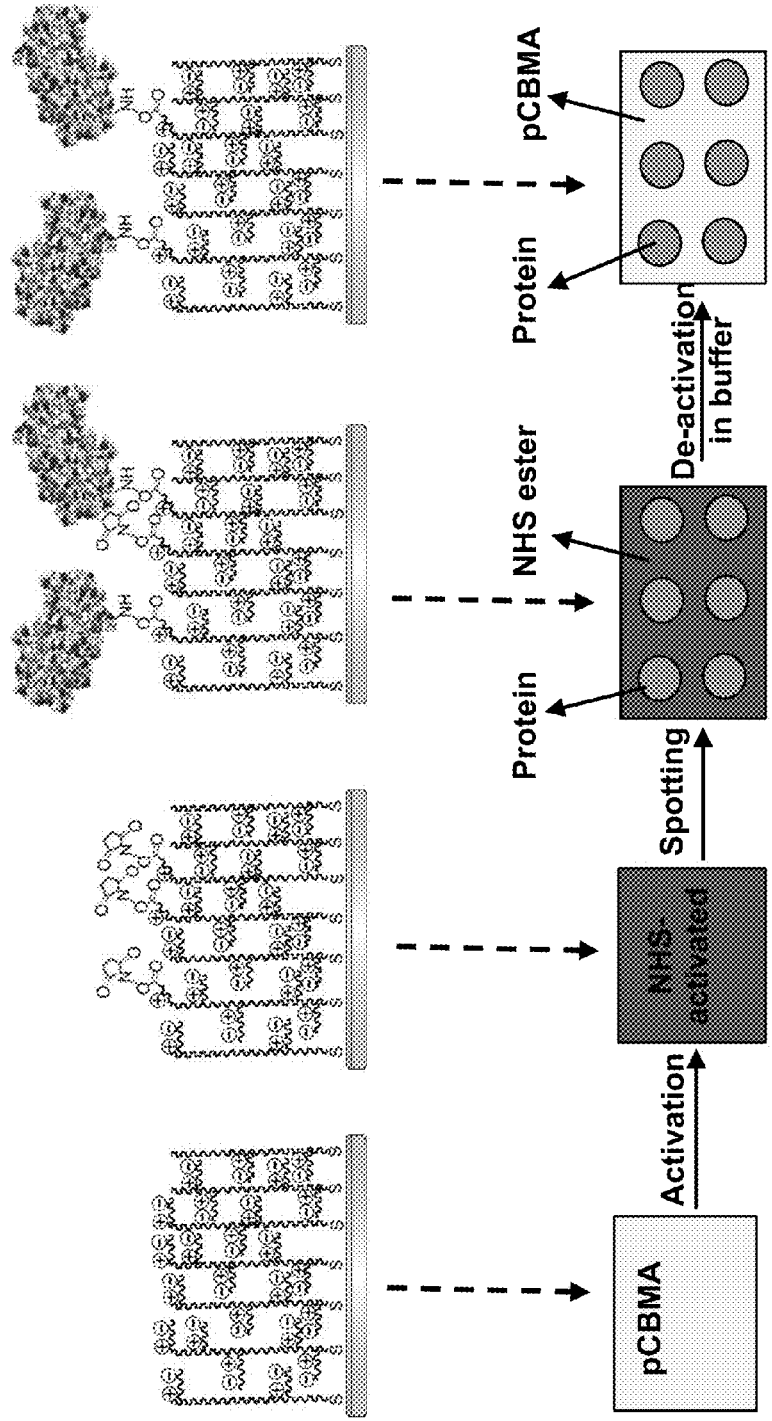
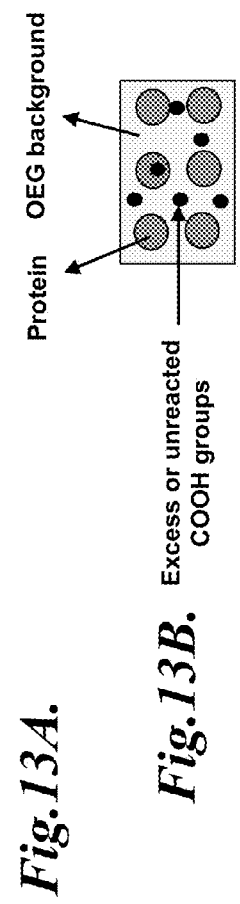
Fig. 13A.
Fig. 13B.

DUAL-FUNCTIONAL NONFOULING SURFACES COMPRISING TARGET BINDING PARTNER COVALENTLY COUPLED TO POLYMER ATTACHED TO SUBSTRATE

CROSS-REFERENCE TO RELATED APPLICATION

This application is a continuation of International Patent Application No. PCT/US2007/089236, filed Dec. 31, 2007, which claims the benefit of U.S. Provisional Application No. 60/882,821, filed Dec. 29, 2006. Each application is expressly incorporated herein by reference in its entirety.

STATEMENT OF GOVERNMENT LICENSE RIGHTS

This invention was made with Government support under Contract No. N000140410409 awarded by the Office of Naval Research. The Government has certain rights in the invention.

BACKGROUND OF THE INVENTION

Surfaces that are resistance to protein adsorption and cell adhesion are critical for the development of biosensors with high specificity and biomaterials with superior compatibility. Currently, oligo(ethylene glycol) (OEG)- or polyethylene glycol (PEG)-based materials such as OEG self-assembling monolayers (SAMs) or poly(OEG methacrylate) are the most commonly used nonfouling materials. Recent studies attribute the nonfouling properties of OEG SAMs to their strong hydration capabilities and well-packed structures. Another commonly used nonfouling material is biomimetic phosphoryl choline (PC)-based materials containing PC headgroups, which are found in the outside layer of cell membranes. Polymers or surfaces modified with PC have been shown to reduce protein adsorption. Recently, applicants have shown that poly(sulfobetaine methacrylate) (polySBMA)-grafted surfaces have low protein adsorption when they are grafted from a surface via the surface-initiated atom transfer radical polymerization (ATRP) method.

Many applications of surface plasmon resonance (SPR) analysis require immobilization of antibodies on the SPR sensor. SPR sensors having immobilized antibodies have been used to detect analytes from complex biological solutions. The elimination of non-specific protein adsorption while maximizing the analyte signal is critical for SPR sensors. Different polymers, most of them with carboxylic acid groups, such as carboxymethylated dextran, carboxymethylated hyaluronic acid, polyacrylic acid and DL-polylactic acid, have been immobilized on the SPR gold surface. However, all these polymers are not protein resistant materials, which means they could adsorb non-specific proteins from complex biological solutions and mask the signal from analytes of interest. Usually, proteins such as BSA have been used to block a surface after the antibody immobilization, which can decrease non-specific binding, but can lead to low efficiency and some unwanted reactions for in vivo testing.

For biosensor or biomaterial applications, it is desirable to have a nonfouling surface or material as a background while presenting an abundance of functional groups for ligand immobilization. Mixed carboxylic (or amino) and hydroxyl-terminated oligo(ethylene glycol) (OEG) self-assembled monolayers (SAMs) or carboxymethyl dextran polymers are currently used in biosensor applications. Copolymers containing decoratable segments and nonfouling polyethylene glycol (PEG) polymers or low-fouling poly(hydroxyethyl methacrylate) or poly(2-methacryloyloxyethyl phosphorylcholine) (polyMPC) segments have been prepared to control cell and tissue responses. However, extra (or unreacted) functional groups can compromise the specificity of a sensor or the biocompatibility of a biomaterial.

Therefore, there is a need for a nonfouling biomaterial with active functional groups for protein or ligand immobilization. The present invention seeks to fulfill these needs and provides further related advantages.

SUMMARY OF THE INVENTION

The present invention provides dual-functional nonfouling surfaces, methods for making dual-functional nonfouling surfaces, and devices that include dual-functional nonfouling surfaces.

In one aspect, the invention provides substrates with nonfouling surfaces having biomolecules covalently coupled thereto. In one embodiment, the substrate has a modified surface that includes (a) a plurality of polymers attached to a surface of a substrate, where each polymer includes a plurality of carboxylic acid groups and a plurality of positive charged groups, and where each polymer is substantially electronically neutral; and (b) a plurality of target binding partners, where the target binding partners are covalently coupled to a plurality of the polymers, and where the target binding partner has affinity toward a target molecule.

In one embodiment, the plurality of polymers are covalently coupled to the surface. In one embodiment, the plurality of polymers are covalently coupled to the surface through a monolayer comprising a plurality of alkylene moieties and form brushes on the surface. In one embodiment, the polymers are poly(carboxybetaines).

In another aspect, the invention provides methods for modifying surfaces to provide nonfouling surfaces having biomolecules covalently coupled thereto. In one embodiment, the method includes covalently coupling a plurality of target binding partners to a plurality of polymers attached to a surface, where the target binding partner has affinity to a target molecule, and where each polymer comprises a plurality of carboxylic acid groups and a plurality of positive charged groups, and where each polymer is substantially electronically neutral.

In one embodiment, covalently coupling the plurality of target binding partners to the plurality of polymers includes forming an amide linkage between the polymers and the target binding partners. In one embodiment, covalently coupling the plurality of target binding partners to the plurality of polymers comprises converting a portion of carboxylic acid groups to activated esters and reacting the activated esters with target binding partners having amino groups. In one embodiment, the activated esters are N-hydroxysuccinimide esters. In one embodiment, the polymers are poly(carboxybetaines).

In another aspect, materials are provided that are nonfouling and that have biomolecules covalently coupled thereto. In one embodiment, crosslinked polymers are provided. In another embodiment, block copolymers are provided.

The crosslinked polymers have a plurality of target binding partners covalently coupled thereto. The crosslinked polymers comprises a plurality of carboxylic acid groups and a plurality of positive charged groups, where the polymers are substantially electronically neutral, and where the target binding partner has affinity toward a target molecule. In one embodiment, the crosslinked polymer is a crosslinked poly (carboxybetaine). In one embodiment, the crosslinked polymer is a hydrogel. Methods for making the crosslinked polymers are also provided.

The block copolymers include a first hydrophilic block and a second hydrophobic block. The block copolymer has a plurality of target binding partners having affinity toward a target molecule covalently coupled thereto. The hydrophilic block comprises a plurality of carboxylic acid groups and a plurality of positive charged groups, and the hydrophilic block is substantially electronically neutral. In one embodiment, the hydrophilic block is a poly(carboxybetaine). In one embodiment, the block copolymer is in the form of a microparticle or a nanoparticle. Methods for making the block copolymers are also provided.

In other aspects, devices that include dual-functional nonfouling surfaces are provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 12A shows BAEC adhesion on inactivated crosslinked poly (CBMA) hydrogel incubated in a fibronectin solution for 24 hours; and FIG. 12B shows BAEC adhesion on EDC/NHS-activated poly(CBMA) hydrogel incubated in a fibronectin solution for 24 hours;

FIG. 13A is a schematic illustration of a representative platform and method of the invention for protein assays, FIG. 13B is a schematic illustration of a conventional platform for protein assays;

DETAILED DESCRIPTION OF THE INVENTION

Figure 1A:
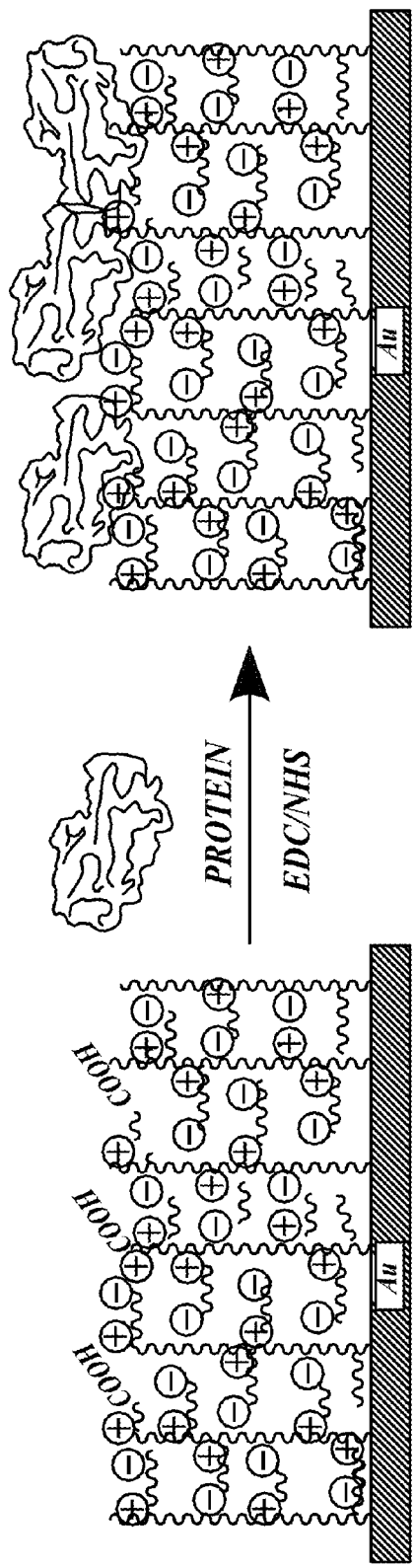
FIGS. 1A and 1B are schematic illustrations of representative dual-functional surfaces of the invention.

The present invention provides dual-functional nonfouling surfaces, methods for making dual-functional nonfouling surfaces, and devices that include dual-functional nonfouling surfaces. The dual-functional surfaces of the invention are surfaces that are nonfouling (e.g., low-fouling or superlow-fouling) surfaces that resist non-specific protein absorption and cell adhesion. The dual-functional surfaces of the invention also include covalently coupled biomolecules (e.g., target binding partners) that impart specific biological activity to the surfaces. Because the dual-functional surfaces of the invention are nonfouling and include immobilized biomolecules, these surfaces that are useful in any method or device that requires sensitive specific binding or specific binding measurement and at the same time requires resistance to non-specific protein binding and cell adhesion. The dual-functional surfaces of the invention are useful in medical diagnostic applications, biomaterials and tissue engineering, and drug delivery.

In one aspect of the invention, dual-functional surfaces are provided. The surfaces have the dual function of resisting or preventing non-specific protein adsorption and cell adhesion and at the same time permitting specific binding to a target molecule.

The surfaces of the invention are nonfouling, which means that the surfaces resist or prevent non-specific protein adsorption and cell adhesion. Non-specific protein adsorption can be measured by determining the level of fibrinogen adsorption (i.e., the amount of fibrinogen that adsorbs to the surface per unit area). The surfaces of the invention adsorb less than about 30 ng/cm$^2$ fibrinogen. In one embodiment, the surfaces have a fibrinogen adsorption less than about 10 ng/cm$^2$; in one embodiment, the surfaces have a fibrinogen adsorption less than about 5 ng/cm$^2$; in one embodiment, the surfaces have a fibrinogen adsorption less than about 3 ng/cm$^2$; and in one embodiment, the surfaces have a fibrinogen adsorption less than about 0.3 ng/cm$^2$.

The nonfouling nature of the surfaces of the invention are due to the materials that make up the surfaces and their packing densities. In the practice of the invention, nonfouling surfaces are prepared from surfaces by coating or covalently coupling a dual-functional material to a surface of a substrate. Thus, the surfaces of the invention are modified surfaces (or coated surfaces).

The dual-functional materials useful for making the surfaces of the invention are materials that impart nonfouling properties to the surfaces and that also include a functional group or groups suitably reactive to immobilize biomolecules (e.g., proteins such as antibodies). Representative functional groups for these dual-functional materials include carboxylic acid groups and amino groups, among others. As described in detail below, in one embodiment, the dual-functional materials are zwitterionic materials that can be attached (e.g., covalently coupled) to a surface and that have terminal carboxylic acid groups. These terminal carboxylic acid groups can be activated for coupling to one or more amino groups present in a biomolecule. In this embodiment, the carboxylic acid groups are converted to active esters (e.g., N-hydroxysuccinimide esters) and then reacted with one or more amino groups (e.g., amino group of a lysine residue of a protein) to form an amide bond thereby immobilizing the protein to the surface to provide a dual-functional surface of the invention.

The nonfouling function of the surface is imparted to the surface by the materials coupled to the surface. As noted above, these materials include zwitterionic materials. Suitable materials useful in making the surfaces include the polymers and copolymers described in PCT/US2006/028988 (Superlow-Fouling Sulfobetaine and Carboxybetaine Materials and related Methods), filed Jul. 25, 2006; PCT/US2007/075409 (Mixed Charge Copolymers and Hydrogels), filed Aug. 7, 2007; and U.S. Application No. 60/989,073 (Cationic Polycarboxybetaine Esters), filed Nov. 19, 2007, each expressly incorporated herein by reference in its entirety.

In one embodiment, the invention provides a substrate having a modified surface that includes
(a) a plurality of polymers attached to a surface of a substrate, wherein each of the polymers comprises a plurality of carboxylic acid groups and a plurality of positive charged groups, and wherein each polymer is substantially electronically neutral; and
(b) a plurality of target binding partners, wherein the target binding partners are covalently coupled to a plurality of the polymers, and wherein the target binding partner has affinity toward a target molecule.

In this embodiment, the materials making up the modified surface includes polymers having a plurality of carboxylic acid groups and a plurality of positive charged groups. The polymers can be homopolymers in which the polymer includes repeating units that include both carboxylic acid groups and positively charged groups. The polymers can also be copolymers that include two types of repeating units: repeating units that include carboxylic acid groups and repeating units that include positively charged groups. The positively charged groups can be pendant groups (i.e., pendant from the polymer backbone) or can be in the polymer backbone. The polymers are substantially electronically neutral. As used herein, the term "substantially electronically neutral" refers to the polymer having substantially equal numbers of positive and negative charges. It will be appreciated that carboxylic acid groups (—CO$_2$H) depicted and described herein are considered to be carboxylate groups (—CO$_2^-$) for the purpose of determining a polymer's electronic neutrality. The electronic neutrality of the polymers making up the modified surfaces of the invention are responsible, in part, for the nonfouling properties of the surfaces of the invention.

In this embodiment, the polymers useful in the invention, and the surfaces modified to include them, include carboxylic acid groups and certain of these carboxylic acid groups are available for further chemical reaction, specifically the immobilization of biomolecules (e.g., target binding partners) to the polymers and, therefore, the modified surface. As noted above, in certain embodiments, biomolecules having available amino groups (—NH$_2$) can be covalently coupled to the polymers' available carboxylic acid groups to immobilize the biomolecule through stable amide linkages (—CONH—). In the practice of the invention, a portion of the polymers having available carboxylic acid groups are activated for coupling and then covalently coupled to the biomolecules to provide surface-immobilized biomolecules. The extent of biomolecules immobilized on the surfaces of the invention can be readily controlled through the reaction conditions (e.g., extent of carboxyl group activation and concentration and amount of biomolecule exposed to the activated surface for immobilization. A schematic illustration of a representative nonfouling surface of the invention having immobilized biomolecules (e.g., target binding partners) is shown in FIG. 1A.

Figure 1B:
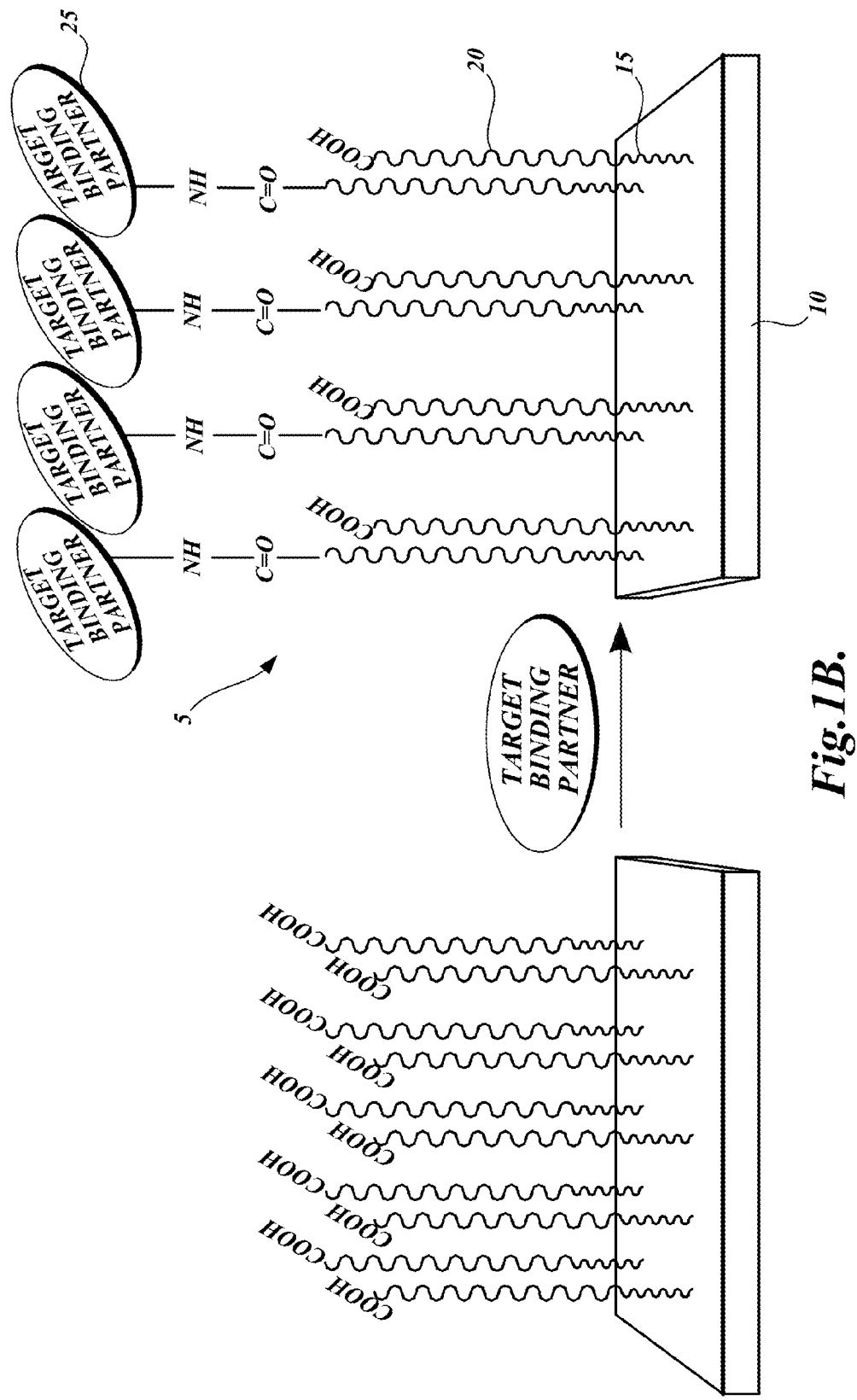

A representative dual-functional surface 5 is illustrated in FIG. 1B. Referring to FIG. 1B, a plurality of polymers 20 having carboxylic acid groups are coupled to substrate 10 through a plurality of linkers 15. The polymers can form a monolayer on the surface of the substrate 10. A portion of the carboxylic acid groups are used to form amide bonds with the amino groups of target binding partners 25 to covalently couple the target binding partners 25 to the polymers 20. The coating of the polymers 20 on the substrate 10 renders the surface 5 nonfouling while the immobilized target binding partners 25 provide binding affinity to a target molecule.

As illustrated in FIG. 1B, the polymers can be attached to the surface directly or through a plurality of linkers. In one embodiment, the substrate of the invention further comprises a monolayer (e.g., self-assembled) covalently coupled to the surface, wherein the monolayer comprises a plurality of alkylene moieties, and wherein the polymers are covalently coupled to the plurality of alkylene moieties.

The binding affinity of a target molecule toward to the surface results from the target binding partners immobilized on the surface. The target binding partner and the target molecule, each termed a binding pair member, form a binding pair. Each binding pair member is a molecule that specifically binds the other member. In one embodiment, the target binding partner has affinity to a target molecule with K$_d$ less than about $10^{-8}$.

A binding pair member can be any suitable molecule including, without limitation, proteins, peptides, proteins, poly- or oligo-saccharides, glycoproteins, lipids and lipoproteins, and nucleic acids, as well as synthetic organic or inorganic molecules having a defined bioactivity, such as an antibiotic, anti-inflammatory agent, or a cell adhesion mediator.

Examples of proteins that can be immobilized on the surfaces of the present invention include ligand-binding proteins, lectins, hormones, receptors, and enzymes. Representative proteins include antibodies (monoclonal, polyclonal, chimeric, single-chain or other recombinant forms), their protein/peptide antigens, protein-peptide hormones, streptavidin, avidin, protein A, proteins G, growth factors and their respective receptors, DNA-binding proteins, cell membrane receptors, endosomal membrane receptors, nuclear membrane receptors, neuron receptors, visual receptors, and muscle cell receptors. Representative oligonucleotides that can be immobilized on the surfaces of the present invention include DNA (genomic or cDNA), RNA, antisense, ribozymes, and external guide sequences for RNAase P, and can range in size from short oligonucleotide primers up to entire genes.

Other target binding partners that bind specifically to a target compound include poly- or oligosaccharides on glycoproteins that bind to receptors, for example, the carbohydrate on the ligand for the inflammatory mediators P-selectin and E-selectin, and nucleic acid sequences that bind to complementary sequences, such as ribozymes, antisense, external guide sequences for RNAase P, and aptamers.

In one embodiment, the target binding partner is an antibody, and the target molecule is an antigen against the antibody. In this embodiment, the surface of the invention specifically binds to the antigen and resists non-specific protein adsorption. In one embodiment, the target binding partner is a protein capable of promoting cell adhesion, and the target molecule is a cell. In this embodiment, the surface of the invention specifically binds to the cell and resists non-specific protein adsorption and non-specific cell adhesion.

A variety of substrate surfaces can be rendered dual-functional using the materials and methods described herein. Representative surfaces that can be rendered dual-functional include metal and metal oxide surfaces, ceramic surfaces, synthetic and natural polymeric surfaces, glass surfaces, fiber glass surface, silicon/silica surfaces, and carbon-based material surfaces. Representative natural polymeric surfaces include collagen, fibrins, and other carbohydrate surfaces suitable for the use of tissue engineering. Representative carbon-based material surfaces include carbon fiber, nanotube, and bulky ball surfaces.

Suitable substrates include those substrates useful in medical diagnostic applications such as biosensors, bioprobes, and biomedical devices including in vivo devices; biomaterials and tissue engineering applications, such as membranes for bioprocesses or bioseparation, implantable devices, prosthetics, and tissue scaffolds; and drug delivery applications, such as particles and nanoparticles.

In one embodiment, the present invention provides a SPR sensor on which zwitterionic polymers were grafted to an SPR surface followed by the immobilization of target binding partners to provide a dual-functional surface.

As noted above, suitable polymers useful for making the modified surfaces of the invention include polymers derived from zwitterionic monomers (as well as monomers that could be converted to zwitterionic monomers, e.g., precursors of zwitterionic monomers). Zwitterionic monomers are electronically neutral monomers that typically include equal numbers of positive and negative charges (e.g., one of each). In the practice of the invention, suitable polymers include any polymer derived from zwitterionic monomers or precursors to zwitterionic monomers that is capable of rendering a surface nonfouling and providing reactive functional groups on the surface for immobilization of a member of a binding pair.

In certain embodiments, the polymers are covalently coupled to the surface through a self-assembly monolayer, wherein the self-assembly monolayer comprises a plurality of alkylene moieties.

In one embodiment, the polymer is a homopolymer prepared from zwitterionic monomers and has the formula:

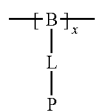

wherein B is selected from the group consisting of

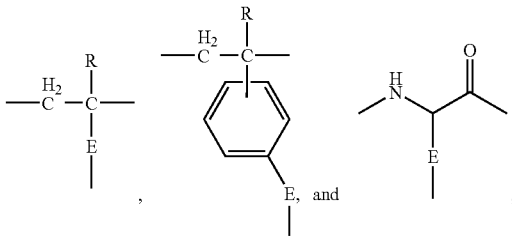

wherein R is selected from the group consisting of hydrogen and substituted or unsubstituted alkyl; and E is selected from the group consisting of substituted or unsubstituted alkylene, —(CH$_2$)$_p$C(O)O—, and —(CH$_2$)$_p$C(O)NR$^2$—, wherein p is an integer from 0 to 12, and R$^2$ is selected from the group consisting of hydrogen and substituted or unsubstituted alkyl;

L is a straight or branched alkylene group optionally including one or more oxygen atoms;

P is selected from the group consisting of

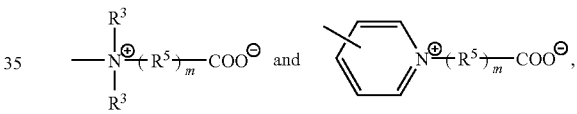

wherein R$^3$ and R$^4$ are independently selected from the group consisting of hydrogen and substituted or unsubstituted alkyl group, R$^5$ is selected from the group consisting of substituted or unsubstituted alkylene, phenylene, and polyether groups, and m is an integer from 1 to 7; and x is an integer from 3 to 1000.

In one embodiment, the polymer is a poly(carboxybetaine). Suitable poly(carboxybetaine)s can be prepared from one or more monomers selected from the group consisting of carboxybetaine acrylates, carboxybetaine acrylamides, carboxybetaine vinyl compounds, carboxybetaine epoxides, and mixtures thereof. In one embodiment, the monomer is carboxybetaine methacrylate. Representative monomers for making carboxybetaine polymers useful in the invention include carboxybetaine methacrylates, such as 2-carboxy-N,N-dimethyl-N-(2'-methacryloyloxyethyl)ethanaminium inner salt; carboxybetaine acrylates; carboxybetaine acrylamides; carboxybetaine vinyl compounds; carboxybetaine epoxides; and other carboxybetaine compounds with hydroxyl, isocyanates, amino, or carboxylic acid groups. In one embodiment, the polymer is a poly(carboxybetaine methacrylate) (poly(CBMA)).

The poly(carboxybetaine) can be prepared by polymerization methods including atom transfer radical polymerization (ATRP), reversible addition fragmentation chain transfer (RAFT) polymerization, and free radical polymerization. Any conventional radical initiators for polymerization may be used.

In another embodiment, the polymer is a homopolymer that has a positive charge in the polymer backbone and a pendant carboxylic acid group and has the formula:

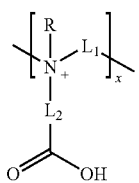

wherein R is selected from the group consisting of hydrogen and substituted or unsubstituted alkyl;

$L_1$ and $L_2$ are independently a straight or branched alkylene group optionally including one or more oxygen atoms; and x is an integer from 3 to 1000.

Figure 2:
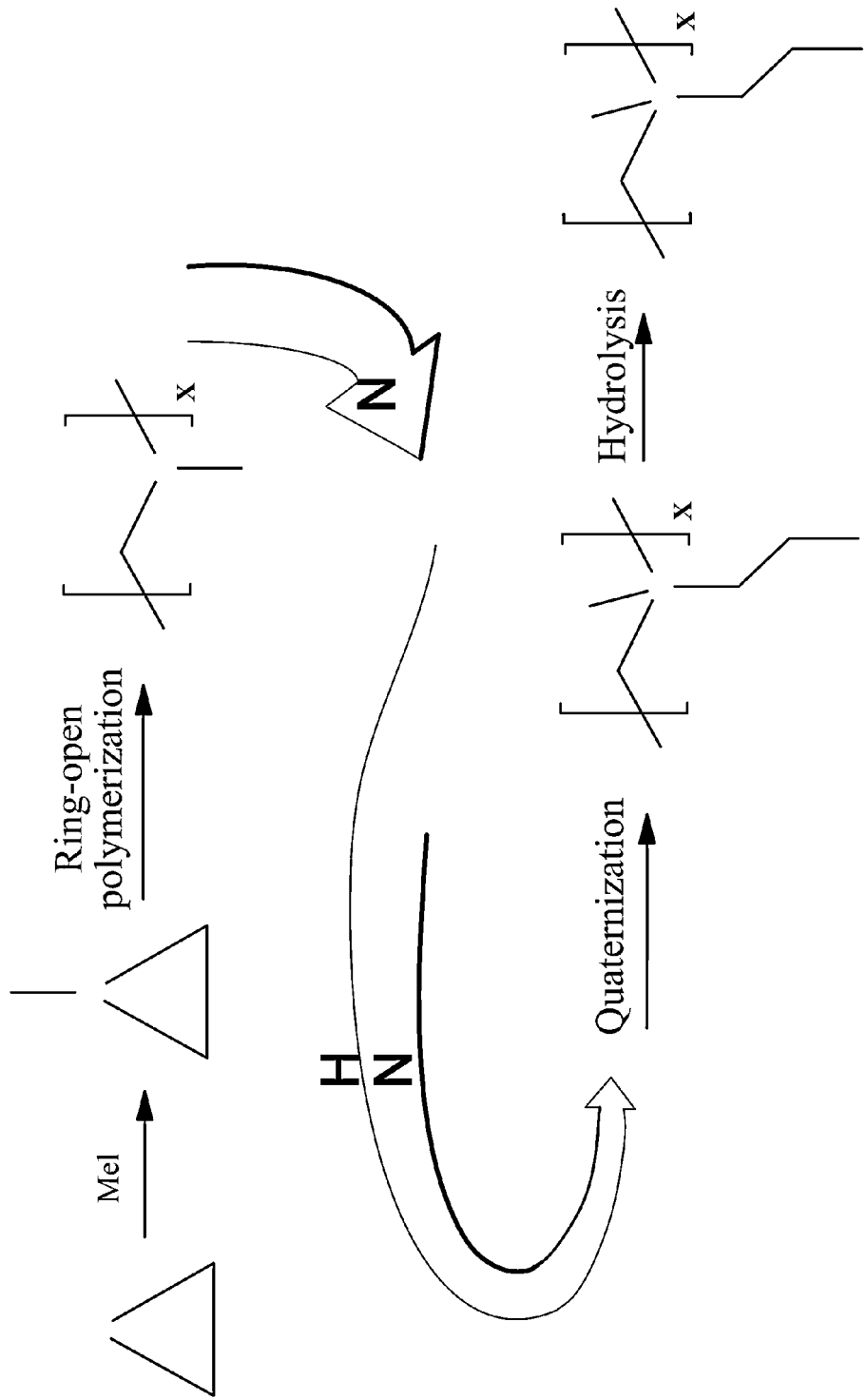
FIG. 2 shows the synthesis of a representative zwitterionic polymer with positively-charged backbone.

A representative zwitterionic polymer 3 with a positively charged backbone can be obtained as shown in FIG. 2. Referring to FIG. 2, polymer 3 can be synthesized with aziridine as the starting material. N-methyl aziridine monomer is obtained by methylation of aziridine. Intermediate polymer 1 having a positively charged backbone is obtained through a ring-open polymerization of N-methyl aziridine monomer. Quaternization of polymer 1 provides intermediate polymer 2 with methyl esters as the pendant group. Hydrolysis of the methyl esters yields the desired zwitterionic polymer 3.

In another embodiment, the polymer is a mixed charge copolymer and has the general formula:

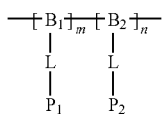

wherein $B_1$ and $B_2$ are independently selected from the group consisting of

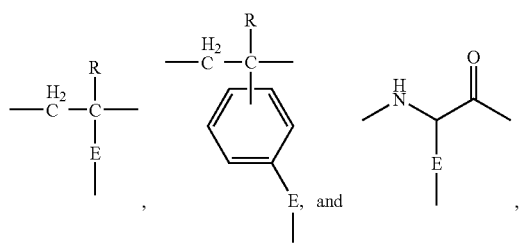

wherein R is selected from the group consisting of hydrogen and substituted or unsubstituted alkyl; and E is selected from the group consisting of substituted or unsubstituted alkylene, $-(CH_2)_pC(O)O-$, and $-(CH_2)_pC(O)NR^2-$, wherein p is an integer from 0 to 12, and $R^2$ is selected from the group consisting of hydrogen and substituted or unsubstituted alkyl;

L is a straight or branched alkylene group optionally including one or more oxygen atoms;

$P_1$ is a positively charged group;

$P_2$ is carboxylic acid group;

m is an integer from 3 to 1000; and n is an integer from 3 to 1000.

In this embodiment, $P_1$ is nitrogen in an aromatic ring or $NR_5R_6$, wherein $R_5$ and $R_6$ are independently substituted or unsubstituted alkyl group.

The positively charged unit ($P_1$ containing unit) can be a derived from a monomer having a positively charged pendant group. Representative monomers that can be used to derive the positively charged unit in the polymers of the present invention include 2-(dimethylamino)ethyl methacrylate, 2-(diethylamino)ethyl methacrylate, [2-(methacryloyloxy)ethyl]trimethylammonium chloride, and N-acetylglucosamine.

The mixed charged copolymers or precursors thereof useful in the present invention can be synthesized directly on a substrate surface. The mixed charged copolymers can be grafted onto a surface via atom transfer radical polymerization (ATRP) from monomers having oppositely charged groups. The copolymers grafted on the surface can form substantially electronically neutral polymer brushes having nonfouling properties.

In one embodiment, the negatively charged unit is derived from 2-carboxyethyl acrylate (CA), and the positively charged unit is derived from 2-(dimethylamino)ethyl methacrylate (DM). In one embodiment, the negatively charged unit is derived from 2-carboxyethyl acrylate (CA), and the positively charged unit is derived from 2-(diethylamino)ethyl methacrylate (DE). In one embodiment, the negatively charged unit is derived from 2-carboxyethyl acrylate (CA), and the positively charged unit is derived from [2-(methacryloyloxy)ethyl]trimethylammonium chloride (TM). In one embodiment, the negatively charged unit is derived from 2-carboxyethyl acrylate (CA), and the positively charged unit is derived from 2-aminoethyl methacrylate hydrochloride (NH2).

For any of the above surfaces, the plurality of polymers can form a monolayer on the surface.

In another aspect, the present invention provides methods for modifying a surface that render the surface nonfouling and having affinity toward a target molecule.

In one embodiment, the method for modifying a surface, includes covalently coupling a plurality of target binding partners to a plurality of polymers that are attached (e.g., covalently coupled) to a surface of a substrate. The target binding partner has affinity to a target molecule. The polymers comprise a plurality of carboxylic acid groups and a plurality of positive charged groups, and wherein the polymer is substantially electronically neutral. The polymers useful in these methods include the polymers described in detail above with regard to the surfaces of the invention. In one embodiment, the polymer is a poly(carboxybetaine).

In certain embodiments, covalently coupling the plurality of target binding partners to the plurality of polymers includes forming an amide linkage between the polymers and the target binding partners. In one embodiment, covalently coupling the plurality of target binding partners to the plurality of polymers includes converting a portion of carboxylic acid groups to activated esters and reacting the activated esters with target binding partners having amino groups. For polymers that have been modified to include available amino groups, covalently coupling the plurality of target binding partners to the plurality of polymers includes converting a portion of carboxylic acid groups of the target binding partners to activated esters and reacting the activated esters with the polymers of the surface having available amino groups.

In one embodiment, the activated esters are N-hydroxysuccinimide esters prepared as described below.

Suitable target binding partners include those described in detail above with regard to the surfaces of the invention.

The invention provides substrates, as described above, having modified surfaces prepared by the methods of the invention.

As noted above, the carboxylic acid groups of the polymers may be activated by forming activated intermediate groups for further coupling with the amino groups of the biomolecule. Any activated form of carboxylic acid groups may be used in the present invention. The representative activated intermediate groups include carbodiimides, carbonyldiimidazoles, uranium salts, isothiocyanates, isocyanates, acyl azides, N-succinimidyl esters (NHS esters), sulfonyl chloride, aldehydes, epoxides arylating groups, imido esters, and anhydrides. In one embodiment, O—(N-succinimidyl)-N,N,N',N'-tetramethyluronium tetrafluoroborate (TSTU) is used to convert the carboxylic acid groups on the polymers to activated uronium salts. In another embodiment, carbodiimides and N-hydroxysuccinimide (EDC/NHS coupling chemistry) are used to convert the carboxylic acid groups on the polymers to activated N-hydroxysuccinimide esters.

In one embodiment, the carboxylic acid groups were converted to activated NHS esters by treating the carboxylic acid groups with N-bromo succinimide (NHS) and N-ethyl-N'-(3-diethylaminopropyl) carbodiimide (EDC) under acidic conditions (e.g., pH 2.5 to 6). The activated NHS esters were coupled with the amino groups of the target binding partner forming amide bonds under basic conditions (e.g., pH 7.4 to 11).

The polymer may be coupled to the surface through alkylene linkers. The grafting of the polymers onto the surface of the substrate through the alkylene linkers may be via any conventional polymerization method such as atom transfer radical polymerization (ATRP), reversible addition fragmentation chain transfer (RAFT) polymerization, and free radical polymerization.

SAMs on substrate surfaces are an excellent platform for surface polymerization. In one embodiment, a radical initiator-terminated self-assembly monolayer (SAM) comprising the alkylene linkers can be formed onto the substrate surface, and the polymers are grafted onto the surface through the radical initiator-terminated self-assembly monolayer. In this method, the substrate surface can be coated with the SAMs terminated with radical initiator, wherein the radical initiators are tethered to the surface through alkylene linkers. The alkylene linkers can be any substituted or unsubstituted alkylene. In one embodiment, the alkylene linker is a C2-C30 alkylene. Polymers are then formed onto the SAMs to provide a layer of nonfouling polymeric coating on the substrate surface. Atom transfer radical polymerization is initiated by the radical initiator at the SAMs terminus.

In one embodiment, a hydroxyl-terminated monolayer having alkylene linkers can be formed onto the substrate surface, which is subsequently converted to a radical initiator terminated monolayer.

Figure 3:
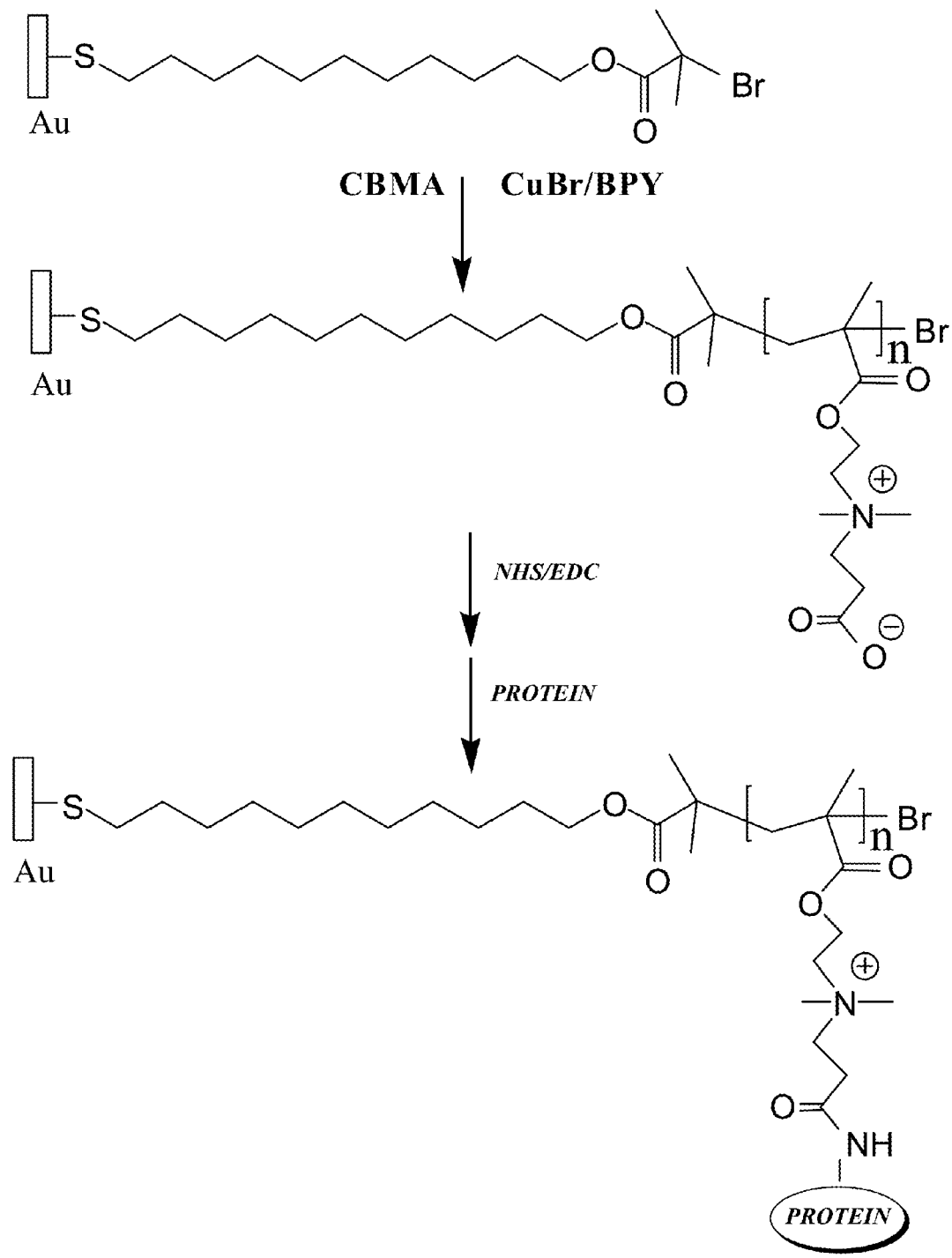
FIG. 3 is a schematic illustration of a representative method for preparing a surface coated with a poly(carboxybetaine methylacrylate) (CBMA) by surface initiated atom transfer radical polymerization (ATRP) and having a protein covalently coupled to the polymer.

A representative dual-functional surface comprising poly(carboxybetaine methacrylate) is described in Example 1 and its preparation illustrated in FIG. 3.

The representative nonfouling surface was prepared by grafting poly(carboxybetaine methacrylate) onto a substrate surface covered with initiators via the surface-initiated ATRP method (FIG. 3). ω-Mercaptoundecyl bromoisobutyrate was synthesized by reacting bromoisobutyryl bromide and mercaptoundecanol. The initiators were immobilized on a gold substrate via self-assembly by soaking the gold substrate in a solution containing w-mercaptoundecyl bromoisobutyrate. One of the CBMA monomers, 2-carboxy-N,N-dimethyl-N-(2'-methacryloyloxyethyl)ethanaminium inner salt, was synthesized by reacting 2-(N,N'-dimethylamino)ethyl methacrylate with β-propiolactone. The CBMA monomers were grafted from radical initiator-terminated SAMs via ATRP. CuBr and 2,2'-bipyridine (BPY) were used as a catalyst and a ligand, respectively. The reaction was kept under mild conditions at room temperature in a mixed solvent of methanol and water. After a typical ATRP polymerization, homogenous carboxybetaine polymer brushes were grafted to the surface. The thickness of the polymer layer was around 10-15 nm as measured by ellipsometry.

Figure 4:
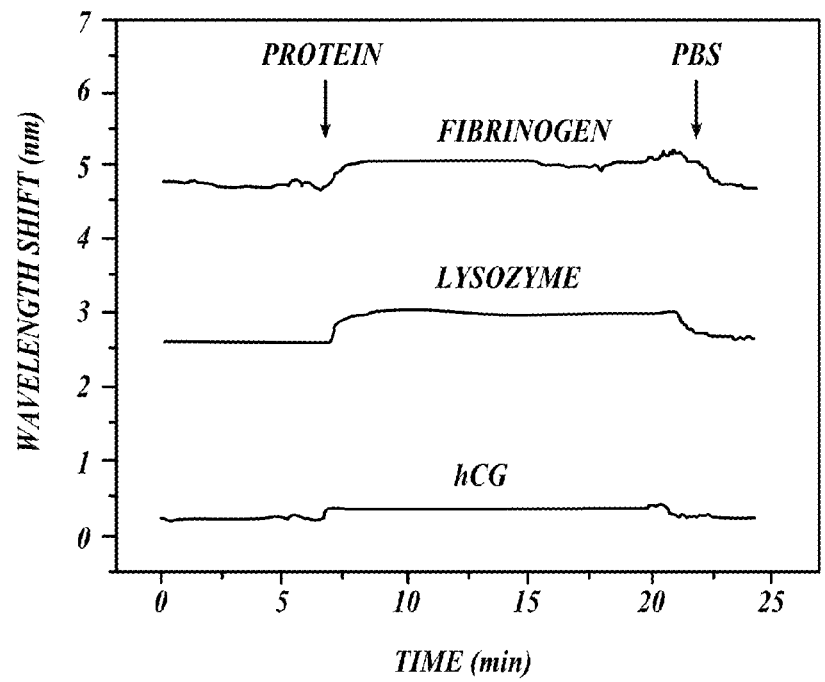
FIG. 4 shows the adsorption of 1 mg/mL fibrinogen, 1 mg/mL lysozyme, and 20 ug/mL anti-hCG from PBS solutions (150 mM and pH 7.4) on poly(CBMA)-grafted surfaces by SPR measurements.

Protein adsorption was measured with a surface plasmon resonance sensor (SPR) based on wavelength interrogation. Protein adsorption is defined as the wavelength shift before protein injection and after buffer wash. The wavelength shift after protein injection is mainly due to the change in the bulk refractive index. The adsorption of three proteins with different sizes and isoelectric points (pI)—human fibrinogen (340 kD, pI=5.5), lysozyme (14 kD, pI=12), and hCG (37 kD, pI=4.5)—on poly(CBMA)-grafted surfaces was shown to decrease to <0.3 ng/cm$^2$ (or a wavelength shift of <0.02 nm, the detection limit of the SPR sensor), as shown in FIG. 4. This level of adsorption is the same as that found for well-packed OEG SAMs or surfaces covered with poly(CBMA) via surface-initiated ATRP. Thus, poly(CBMA)-grafted surfaces are highly resistant to non-specific protein adsorption.

Following monolayer formation on the surface, a representative target binding partner, a monoclonal antibody (mAb) to human chorionic gonadotropin (hCG) was covalently immobilized onto the surface covered with poly(CBMA) brushes by reacting the amines of the mAb to the carboxyl groups of the poly(CBMA) via EDC/NHS coupling chemistry as shown in FIG. 3.

Figure 5:
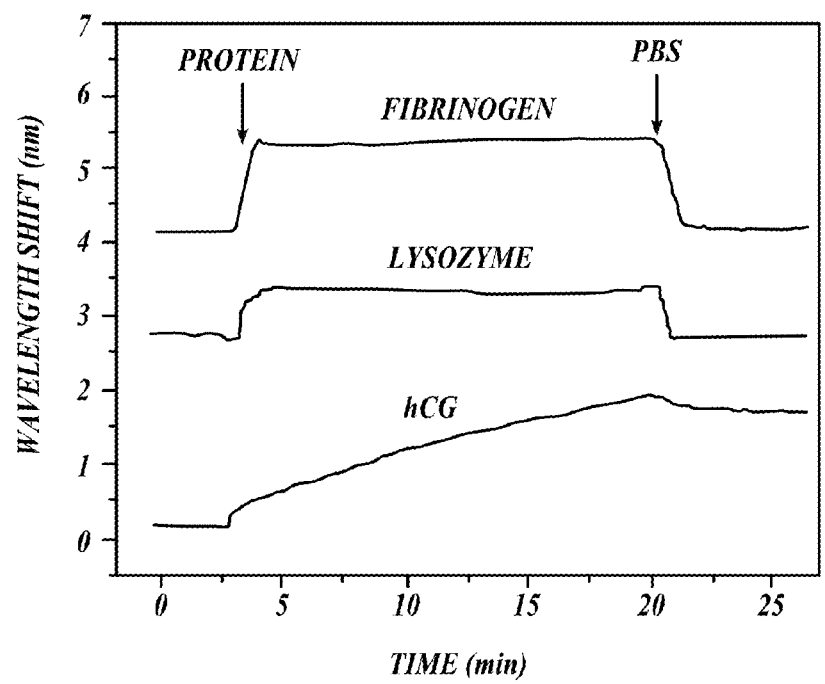
FIG. 5 shows the adsorption of 1 mg/mL fibrinogen, 1 mg/mL lysozyme, and 20 ug/mL anti-hCG from PBS solutions (150 mM and pH 7.4) on poly(CBMA)-grafted surfaces with immobilized anti-hCG by SPR measurements.
Figure 6:
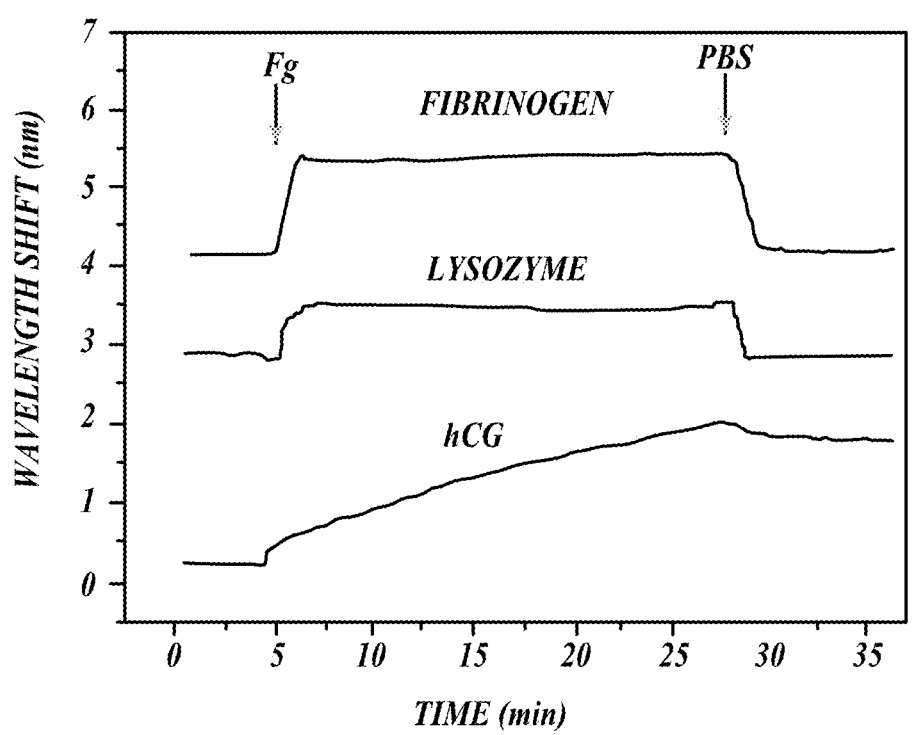
FIG. 6 shows the adsorption of 1 mg/mL fibrinogen, 1 mg/mL lysozyme, and 40 ug/mL anti-hCG from PBS solutions (150 mM and pH 7.4) on poly(CBMA)-grafted surfaces with immobilized anti-hCG by SPR measurements.

After the immobilization, unreacted NHS was removed with ethanolamine. The SPR response after an injection of hCG shows that the adsorbed amount of protein is much greater on the poly(CBMA)-grafted surface with immobilized anti-hCG than on the control poly(CBMA)-grafted surfaces without the immobilized mAb. FIG. 5 shows the protein adsorption on the poly(CBMA)-grafted surface with immobilized anti-hCG when the surface is treated with PBS solution containing 1 mg/mL fibrinogen, 1 mg/mL lysozyme, and 20 μg/mL hCG for 22 min. FIG. 6 shows the protein adsorption on the poly(CBMA)-grafted surface with immobilized anti-hCG when the surface is treated with PBS solution containing 1 mg/mL fibrinogen, 1 mg/mL lysozyme, and 40 μg/mL hCG for 22 min. The wavelength shift of the SPR spectra is 1.6 nm, corresponding to hCG adsorption of about 24 ng/cm$^2$. At the same time, the adsorption of both lysozyme and fibrinogen remains the same on both surfaces (less than 0.3 ng/cm$^2$), indicating that the surface is still nonfouling after anti-hCG immobilization. Thus, the poly(CBMA)-grafted surface with an immobilized anti-hCG represents a dual-functional surface with both resistance to non-specific protein adsorption and binding to a specific protein.

The activation of carboxylic acid groups of poly(carboxybetaine) on the surface is important for the subsequent immobilization of target binding partners. To achieve high protein immobilization level, the conditions for the activation of carboxylic acid groups and the immobilization of the target binding partners need to be optimized.

As shown in Example 2, the optimal activation of carboxylic acid groups of the polymers using NHS/EDC method (the greatest amount of NHS esters) was achieved in situ using water/HCl, pH 3.3 as a solvent. The surface coated with poly(carboxybetaine methylacrylate) was activated by injection of freshly prepared solution of NHS (0.05M) and EDC (0.2M) at 30° C. Two different antibodies, monoclonal antibody against activated cell leukocyte adhesion molecule (anti-ALCAM) and polyclonal antibody against *Salmonella* (anti-Salm), were immobilized into different spots of the activated CBAA surface under various pH conditions with antibody concentration of 50 ug/mL. Then, the non-covalently bound ligands were removed from the surface.

Figure 7:
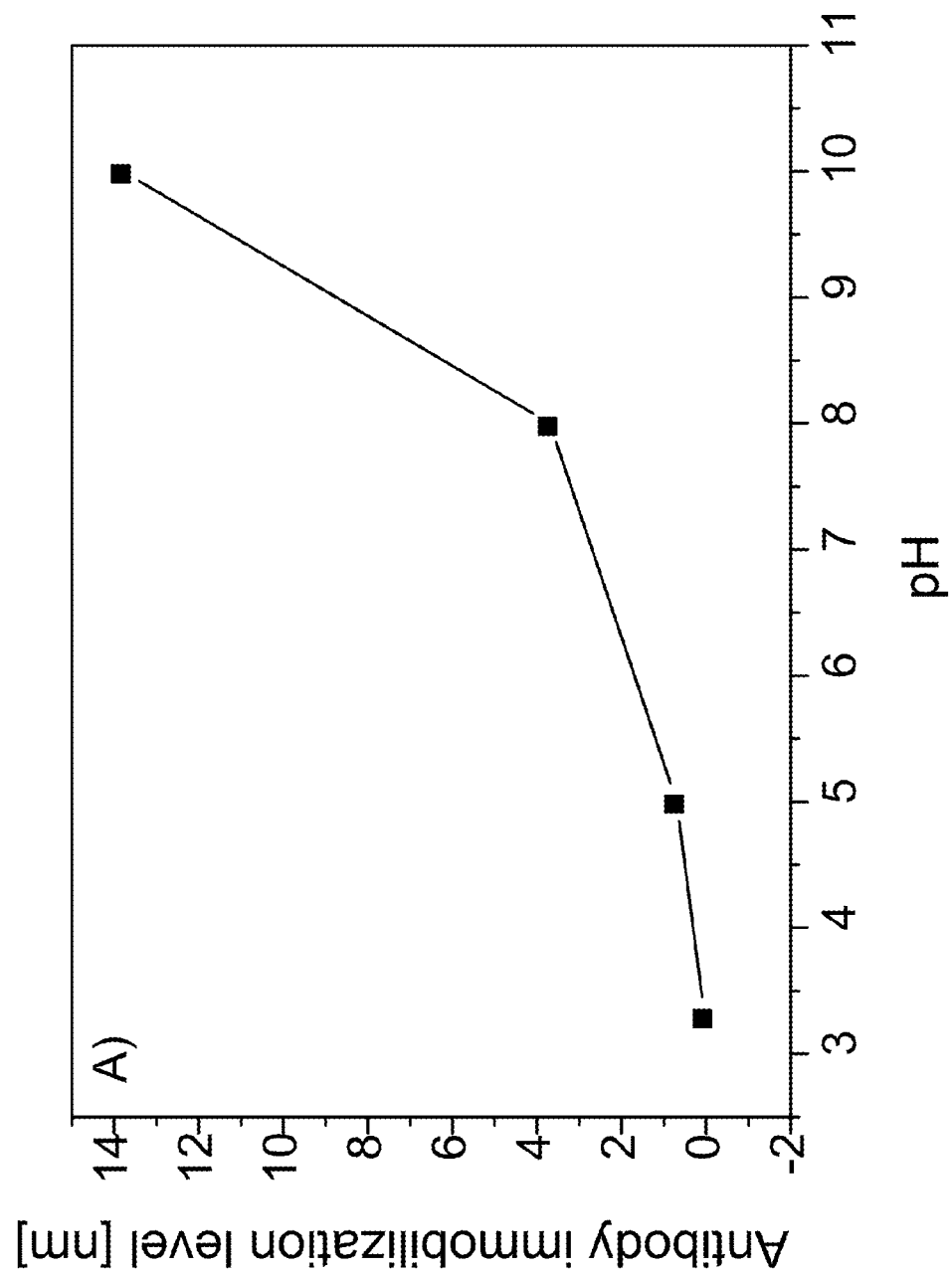
FIG. 7 shows the effect of antibody immobilization buffer on final antibody immobilization level on an activated poly (CBMA) coated surface.
Figure 8:
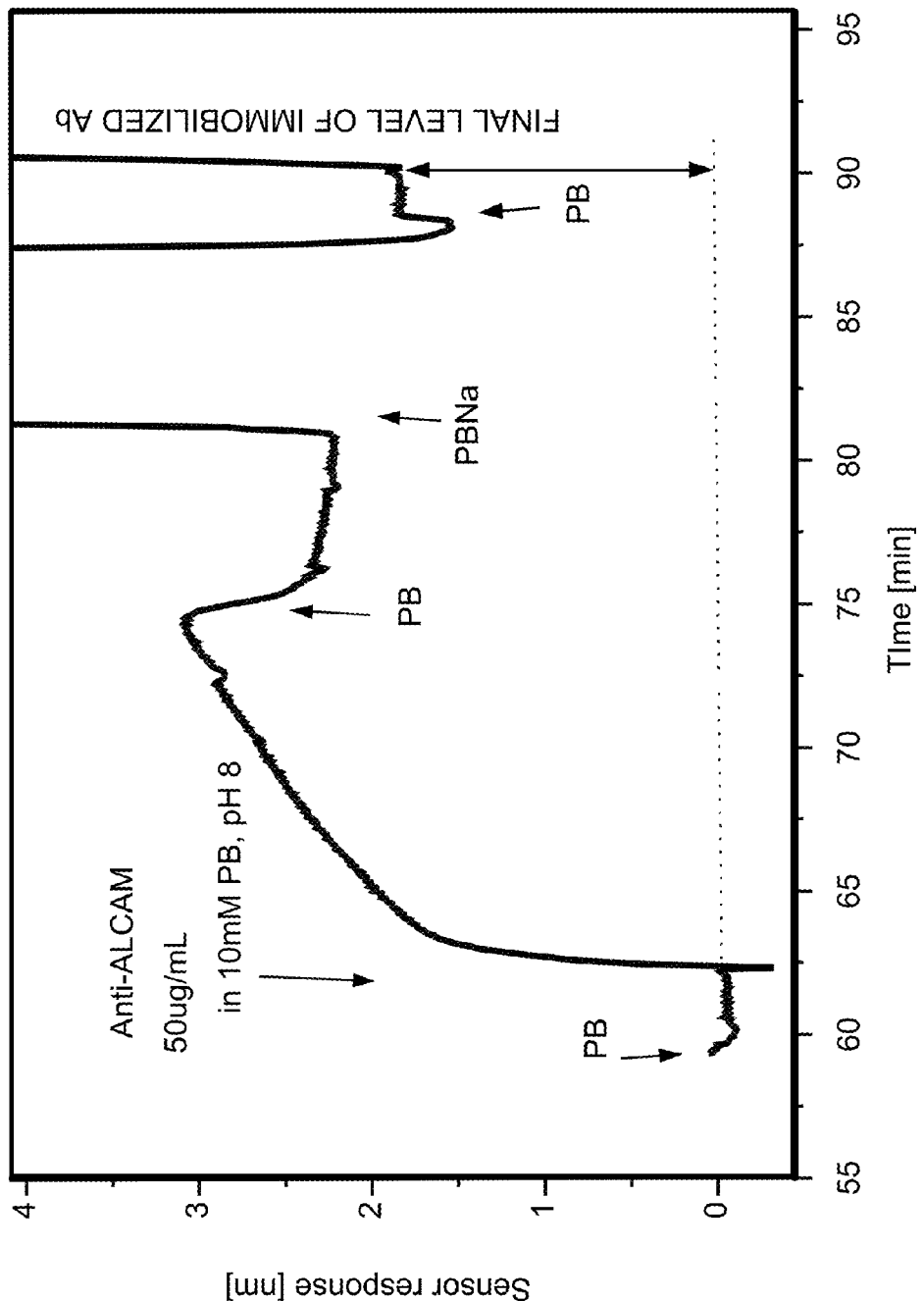
FIG. 8 shows a typical response to immobilization of antibody at pH 8.0 on a representative poly(CBMA) coated surface.
Figure 9:
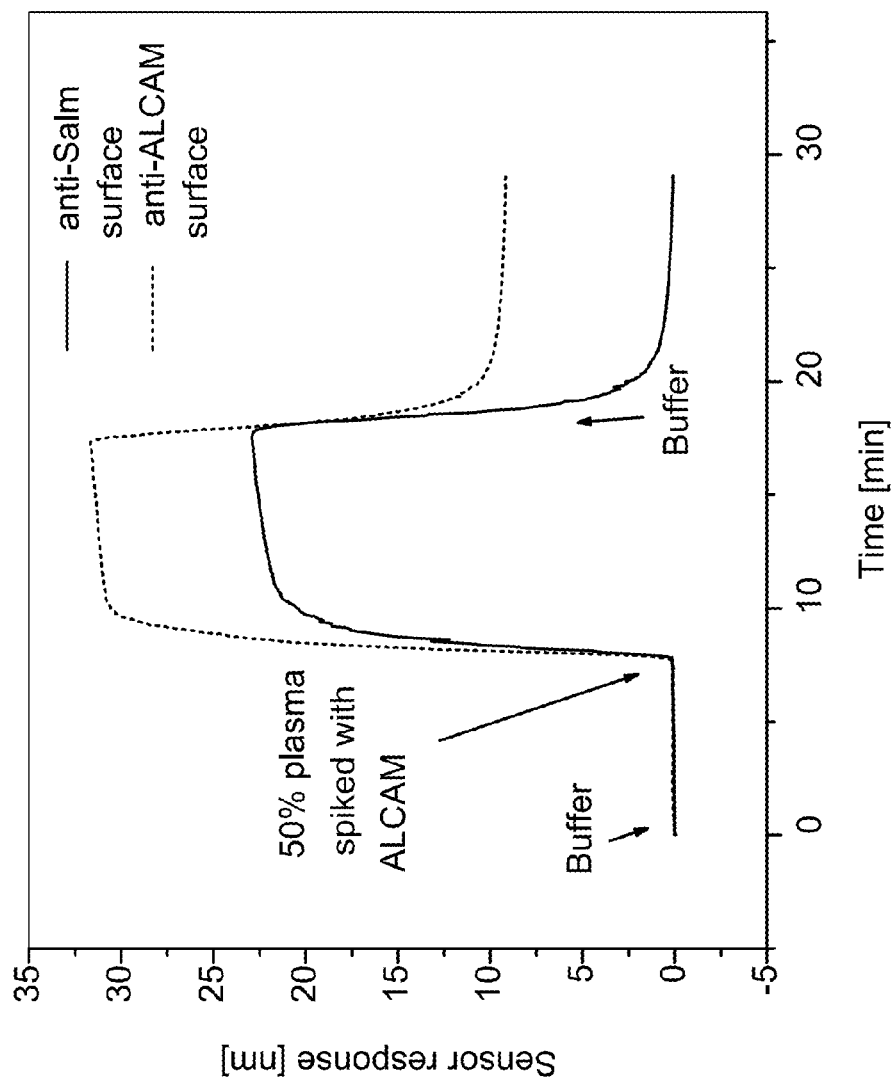
FIG. 9 compares the detection of activated cell leukocyte adhesion molecule (ALCAM) on a surface immobilized with antibodies against activated cell leukocyte adhesion molecule (anti-ALCAM) and a reference surface with immobilized antibodies against *Salmonella* (anti-Salm) in 50% plasma.

The effect of pH on antibody immobilization is shown in FIG. 7. It is apparent from FIG. 7 that higher pH of immobilization condition corresponds to higher amount of immobilized protein. A typical response to immobilization of antibody at pH 8.0 is shown in FIG. 8. FIG. 9 compares the detection of ALCAM on an anti-ALCAM immobilized surface and a reference surface with immobilized anti-Salm in 50% plasma.

The activation of the carboxylic acid groups of poly(carboxybetaine methylacrylate) may be achieved by treating the carboxylic acid groups with TSTU as described in Example 3. A custom-built four-channel spectroscopic surface plasmon resonance sensor was used to monitor poly(CBAA) surface functionalization.

Poly(CBAA) chips were first prepared in the form of Poly (CBAA) esters via ATRP method. The poly(CBAA)-ester surface is then hydrolyzed to achieve zwitterionic nonfouling poly(CBAA) surface. A sensor chip surface with grafted poly (CBAA) esters was washed with MilliQ water, dried with filtered air and mounted into the SPR sensor. The hydrolysis was performed in situ by flowing with 0.1M NaOH, pH 12 for 2 hours along the poly(CBAA) surface. The effectiveness of hydrolysis was monitored by injection of highly surface-sticking protein (fibrinogen) with concentration of 1 mg/mL in phosphate buffered saline (PBS), pH 7.4. It was found that 2 hours was sufficient time to fully hydrolyze the poly (CBAA) ester surface.

The zwitterionic poly(CBAA) surface was immersed in solution of TSTU (5 mg/mL) in DMF for 2 hours. After that, the surface was washed with ethanol and dried with filtered air. The chip was immediately mounted into the SPR sensor. The model system of two antibodies was used to demonstrate functionalization of the surface-grafted poly(CBAA). Antibody against activated cell leukocyte adhesion molecule (anti-ALCAM) was immobilized into the measuring channel and antibody against *Salmonella* (anti-Salm) was immobilized into the reference channel. Immobilization was performed in situ in 10 mM sodium acetate buffer, pH 5.0. Antibody concentration was consecutively 10 ug/mL and 50 ug/mL, incubation time was 15 minutes.

Figure 10:
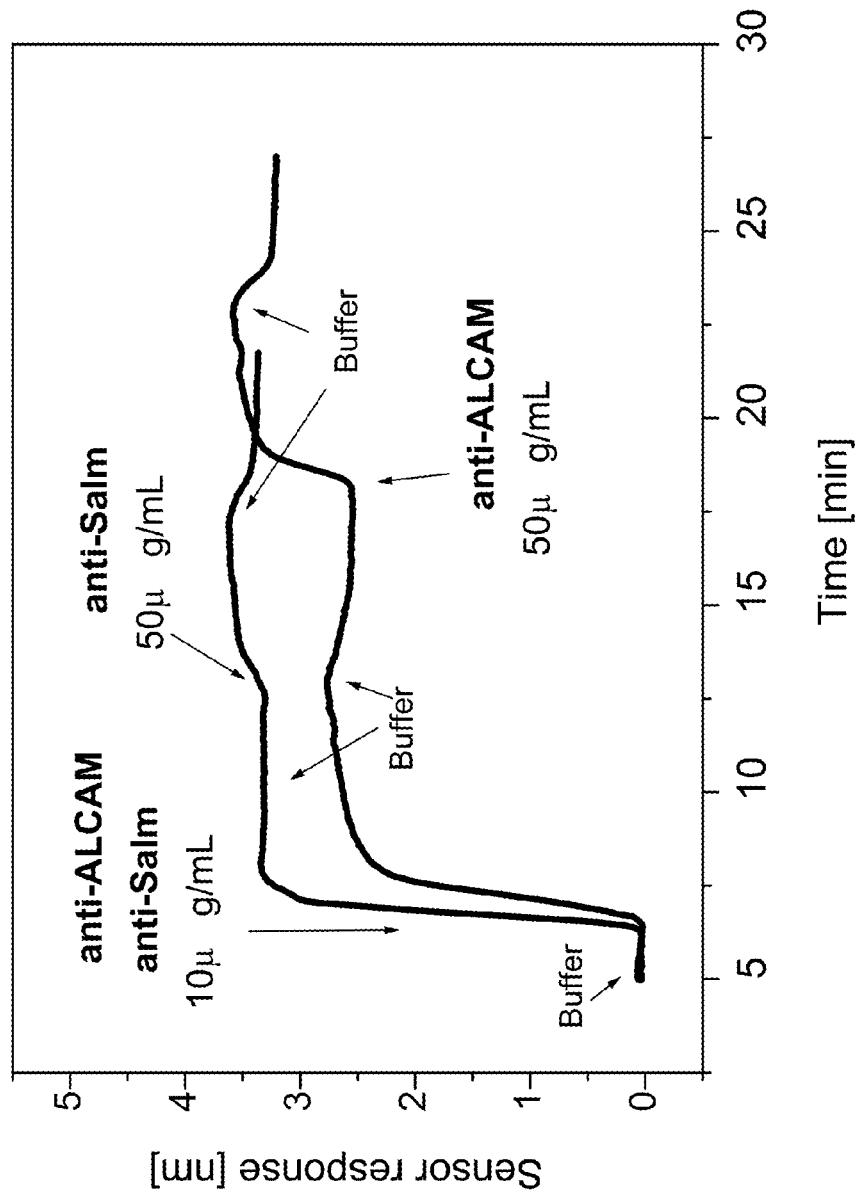
FIG. 10 is a sensorgram corresponding to the immobilization of anti-ALCAM and anti-Salm onto TSTU-activated poly(CBAA)-grafted surface with the running buffer having a antibody concentration of 10 ug/mL and 50 ug/mL, consecutively, in 10 mM sodium acetate at pH 5.0.
Figures 11A, 11B:
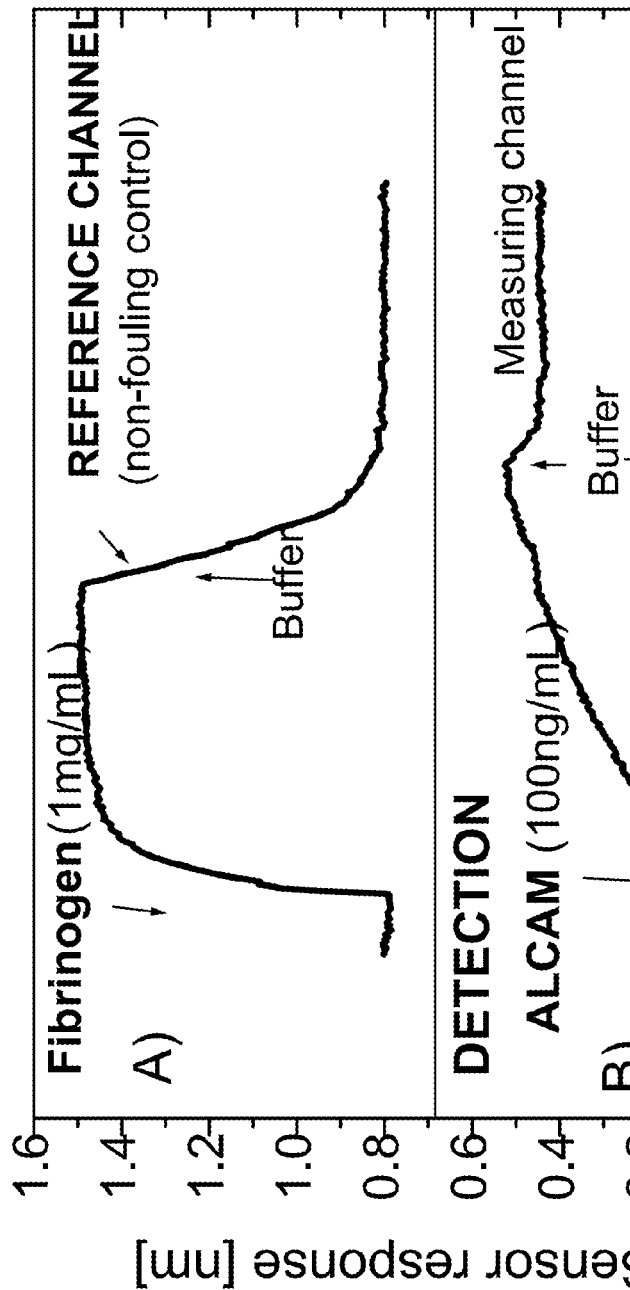
FIG. 11A shows the control of nonfouling properties of poly(CBAA) after deactivation of residual carboxylic acid groups by injection of fibrinogen in PBS with concentration of 1 mg/mL.
FIG. 11B compares the sensor response to ALCAM binding (100 ng/mL) in measuring (anti-ALCAM) and reference (anti-Salm) channels.

FIG. 10 shows sensor response to immobilize ALCAM and *Salmonella* antibodies on the surface of a poly(CBAA) sensor activated with TSTU. Running buffer was 10 mM sodium acetate, pH 5.0 with the concentration of antibody as 10 ug/mL and 50 ug/mL, consecutively. FIG. 11 shows the detection of ALCAM using the anti-ALCAM immobilized surface and low background noise (or low non-specific binding) using a non-targeted antigen, fibrinogen. Residual NHS-esters were transformed back to carboxylate groups by flowing 10 mM phosphate buffer, 150 mM NaCl, pH 8.5 for 5 hours. Fibrinogen with concentration of 1 mg/mL was injected into reference channel to check for the effectiveness of hydrolysis and super nonfouling properties (FIG. 11A). Detection of ALCAM antigen was performed then in PBS buffer. A solution of ALCAM with concentration of 100 ng/mL was injected over the measuring and reference channel for 10 minutes. FIG. 11B shows sensor response to ALCAM binding in the measuring (anti-ALCAM) and reference (anti-Salm) channels. ALCAM antigen was bound specifically to the anti-ALCAM surface. These results demonstrate that deactivation process was successful and functionalized poly (CBAA) surface kept its super nonfouling properties while the biological activity of anti-ALCAM was preserved.

In other aspects, the invention provides materials having target binding partners immobilized thereto that are useful for rendering surfaces nonfouling. These materials are polymeric materials that can be used to coat surfaces. These materials can be used independently of substrate surfaces. The materials can be formed into particles and used in particulate form. Representative materials of the invention include crosslinked polymers (e.g., hydrogels) having target binding partners immobilized thereto and block copolymers (e.g., microparticles and nanoparticles) having target binding partners immobilized thereto.

In one embodiment, the present invention provides a crosslinked polymer (e.g., hydrogel) having a plurality of target binding partners covalently coupled thereto.

In one embodiment, the crosslinked polymer has a plurality of target binding partners covalently coupled thereto. The crosslinked polymers have a plurality of carboxylic acid groups and a plurality of positive charged groups, and are substantially electronically neutral. The target binding partner has affinity toward a target molecule.

The polymers making up the crosslinked polymers include those described above in regard to the surfaces of the invention.

In one embodiment, the crosslinked polymer is a crosslinked poly(carboxybetaine) hydrogel. The carboxybetaine can be prepare from one or more monomers selected from the group consisting of carboxybetaine acrylates, carboxybetaine acrylamides, carboxybetaine vinyl compounds, carboxybetaine epoxides, and mixture thereof. In one embodiment, the monomer is carboxybetaine methacrylate.

Representative crosslinked polymers can be prepared from positively charged compounds including aminoethyl methacrylate hydrochloride (NH2), (2-(dimethylamino)ethyl methacrylate (DM), 2-(diethylamino) ethyl methacrylate (DE), and 2-(methacryloyloxy)ethyl trimethylammonium chloride (TM), and negatively charged compounds including 2-carboxyethyl acrylate (CA).

In one embodiment, the crosslinked polymer NH2/CA has the negatively charged unit derived from 2-carboxyethyl acrylate (CA) and the positively charged unit derived from 2-aminoethyl methacrylate hydrochloride (NH2). In one embodiment, the crosslinked polymer DM/CA has the negatively charged unit derived from 2-carboxyethyl acrylate (CA) and the positively charged unit derived from 2-(dimethylamino)ethyl methacrylate (DM). In one embodiment, the crosslinked polymer DE/CA has the negatively charged unit derived from 2-carboxyethyl acrylate (CA) and the positively charged unit derived from 2-(diethylamino)ethyl methacrylate (DE). In one embodiment, the crosslinked polymer TM/CA has the negatively charged unit derived from 2-carboxyethyl acrylate (CA) and the positively charged unit derived from [2-(methacryloyloxy)ethyl]trimethylammonium chloride (TM).

Immobilization of the target binding partner to the crosslinked polymers can be carried out as described above for the surfaces of the invention. The target binding partner can be immobilized onto the polymer by, for example, reacting the amino groups of the protein to the carboxylic acid groups available on the surface of crosslinked polymer. The target binding partners include those described above in regard to the surfaces of the invention.

The present invention provides methods for making crosslinked polymers having a plurality of target binding partners covalently coupled to the polymers.

In one embodiment, the method for making a surface-modified crosslinked polymer includes:

(a) copolymerizing one or more monomers and a crosslinking agent to provide a crosslinked polymer, wherein the crosslinked polymer comprises crosslinked polymers having a plurality of carboxylic acid groups and a plurality of positive charged groups, wherein the crosslinked polymers are substantially electronically neutral; and (b) covalently coupling a plurality of target binding partners to the crosslinked polymer.

In the method, covalently coupling a plurality of target binding partners to the crosslinked polymer can be carried out using the materials and methods described above for the preparation of the surfaces of the invention.

Suitable crosslinking agents include those commonly used in vinyl-type polymer crosslinking. In one embodiment, the crosslinking agent is tetraethylene glycol dimethacrylate.

A representative crosslinked polymer hydrogel of the invention, a crosslinked poly(CBMA) hydrogel, was prepared as described in Example 4. The transparent hydrogel was prepared by adding carboxybetaine methacrylate monomer into tetraethylene glycol dimethacrylate (TEGDMA) followed by free radical polymerization initiated by sodium metabisulfite and ammonium persulfate. After polymerization, the gel was prepared according to the well-established procedure known in the art to remove residual chemicals. The poly(CBMA) hydrogel was found to be noncytotoxic and contained less than 0.06 units (EU)/mL of endotoxin using a Limulus amebocyte lysate (LAL) endotoxin assay kit (Cambrex Bioscience, Walkersville, Md.). The hydrogel was punched into disks.

Figure 12A:
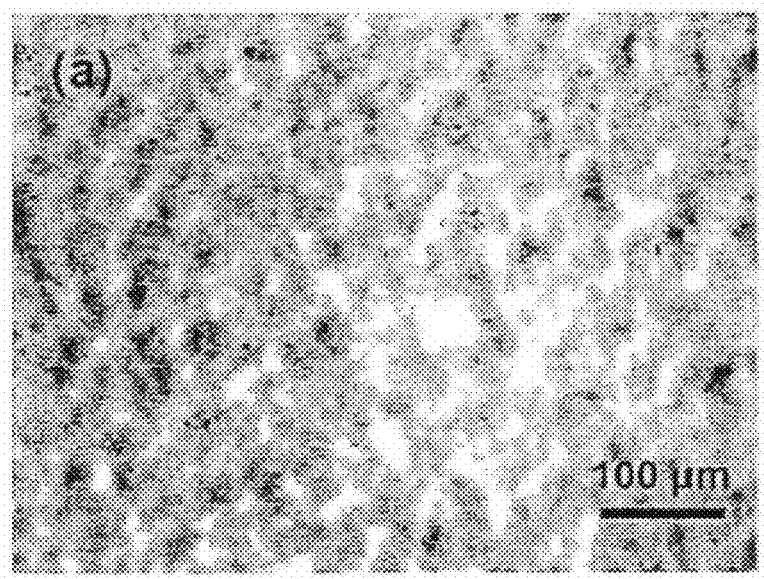
FIGS. 12A and 12B are microscopic images of bovine aortic endothelial cell (BAEC) adhesion after 24 h.
Figure 12B:
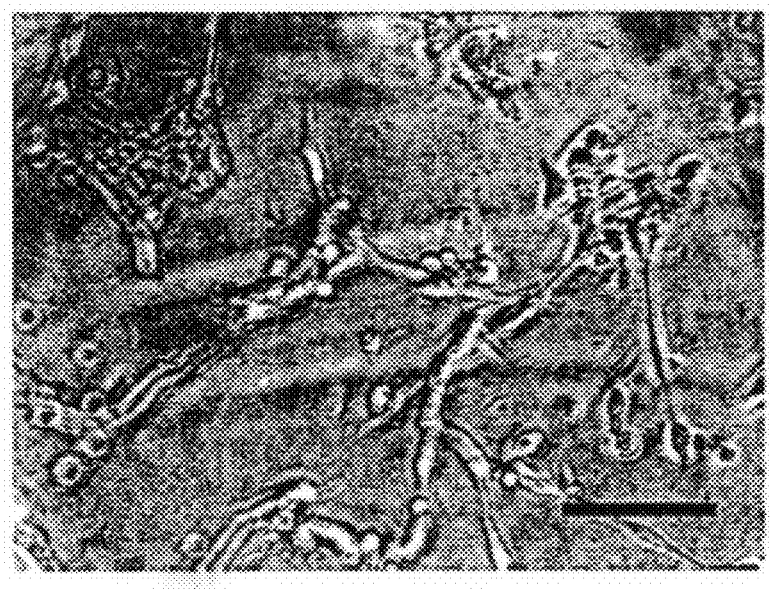

The crosslinked poly(CBMA) hydrogel was then evaluated for its dual functionality. The poly(CBMA)-based hydrogel was modified by EDC/NHS activation followed by fibronectin conjugation to provide a modified hydrogel decorated with immobilized fibronectin. The fibronectin is a protein capable of promoting cell adhesion. Following protein conjugation, bovine aortic endothelial cells (BAECs) were cultured on both fibronectin-modified hydrogel disks and the hydrogel disks without EDC/NHS activation. Cell morphology was observed between 2 h and 3 days of cultivation. While there were no adhered cells on the poly(CBMA) hydrogel disks without EDC/NHS activation as shown in FIG. 12A, BAECs were observed on the surfaces that were activated with EDC/NHS before the fibronectin conjugation (FIG. 12B). These results show that the poly(CBMA) hydrogel itself is highly resistant to cell adhesion and can be readily immobilized with proteins or other ligands.

In another embodiment, the invention provides block copolymers having a plurality of target binding partners covalently coupled thereto. The block polymers have a first hydrophilic block and a second hydrophobic block. The hydrophilic block includes a plurality of carboxylic acid groups and a plurality of positive charged groups, and is substantially electronically neutral. Covalently coupling a plurality of target binding partners to the block copolymers can be carried out using the materials and methods described above for the preparation of the surfaces and crosslinked polymers of the invention. These block copolymers can be advantageously used in the form of microparticles and nanoparticles.

The diblock copolymers have the general formula [hydrophobic monomer]$_l$–block-[hydrophilic monomer]$_m$ copolymer, where l is an integer from 10-30 and m is an integer from 10 to 100. In one embodiment, the hydrophilic block is a poly(carboxybetaine).

In one embodiment, well-defined diblock copolymers containing carboxybetaine moieties, such as poly(CBMA), with a hydrophobic moiety, such as poly(propylene oxide) (PPO), are adsorbed onto surfaces coated with alkyl-terminated SAMs, such as methyl (CH$_3$)-terminated SAMs. For this embodiment, the hydrophobic polymer segment binds to the hydrophobic surface and the hydrophilic sulfobetaine moiety is exposed to, for example, an aqueous solution in contact with the surface.

The diblock copolymers of the invention can be composed of a variety of carboxybetaine-based hydrophilic portions having varied length and any suitable hydrophobic portion with varied length, and the diblock copolymers can be prepared by any suitable methods of polymerization.

Representative monomers for making carboxybetaine polymers useful in the invention include carboxybetaine methacrylates, such as 2-carboxy-N,N-dimethyl-N-(2'-methacryloyloxyethyl)ethanaminium inner salt; carboxybetaine acrylates; carboxybetaine acrylamides; carboxybetaine vinyl compounds; carboxybetaine epoxides; and other carboxybetaine compounds with hydroxyl, isocyanates, amino, or carboxylic groups. Any hydrophobic polymer chains could be used as the hydrophobic moiety for the copolymer of the invention. Representative hydrophobic moieties include poly(propylene oxide) (PPO), polymethacrylates, polyacrylates, polyacrylamides, polyesters, polyethers, polyurethanes, and polyamides.

In one embodiment, two block copolymers can be used together. In one embodiment, the first diblock copolymer comprises a [hydrophobic monomer]$_l$-block-[hydrophilic monomer]$_m$ copolymer. In one embodiment, the first diblock copolymer comprises a [propylene oxide]$_l$-block-[carboxybetaine methacrylate]$_m$ copolymer. In one embodiment, the second diblock copolymer comprises a [hydrophobic monomer]$_l$-block-[hydrophilic monomer]$_n$ copolymer. In one embodiment, the second diblock copolymer comprises a [propylene oxide]$_l$-block-[carboxybetaine methacrylate]$_n$ copolymer. For these polymers l is an integer from 10-30, m is an integer from 10-100, n is an integer from 10-50, and m is greater than n.

The materials and methods of the invention can be used advantageously in a variety of applications. In one embodiment, the materials and methods of the invention can be used to prepare protein arrays for performing protein assays.

Non-specific adsorption of proteins is routinely observed on traditional protein arrays, leading to high background levels. The problem is especially noticeable when complex protein solutions are used, such as blood, tissue or cell lysate. Non-specific adsorption of non-target proteins compromises the specificity of any sensor surface, and makes the results less reliable. The advantages of using a surface platform for protein arrays made from the materials and by the methods of the invention include (a) excellent nonfouling characteristics in blood serum and plasma, (b) abundant functional groups for protein immobilization, and (c) activated surfaces for protein immobilization can be automatically de-activated back to a superlow fouling background. None of the existing surface chemistries have all of these unique properties together.

FIG. 13A is a schematic illustration of an array (a pCBMA-based surface platform for protein arrays) using the materials and the methods of the invention. A gold coated surface or a glass slide is grafted with pCBMA via ATRP. The surface (i.e., the carboxylic acid moiety of the zwitterionic carboxybetaine group) can be activated using the two-step NHS/EDC chemistry described above. Proteins are then spotted directly onto the surface using a spotter. The chip is automatically de-activated with buffer where the activated carboxylic acid moiety returns to its original carboxylate ion, leading to a nonfouling background of Pcbma. FIG. 13B is a schematic illustration of conventional mixed COOH/OH OEG SAM surface platform for protein arrays and the only final stage after protein immobilization is shown. Nonspecific protein binding from complex medium like blood serum or plasma is very sensitive to the existence of the excess or unreacted COOH groups on the protein array surface. The inherent problem for conventional surface chemistries is that they contain two separate functional and nonfouling groups.

The preparation of a representative protein array and its use in performing protein assays is described in Example 5.

The following is a listing of abbreviations used herein.

Abbreviations

AIBN Azobisisobutylonitrile
ALCAM Activated cell leukocyte adhesion molecule
ATRP atom transfer radical polymerization
BAEC Bovine aortic endothelial cell
C12 Lauryl methacrylate
CA 2-Carboxyethyl acrylate
CBMA Carboxybetaine methylacrylate
DE 2-(Diethylamino) ethyl methacrylate
DM 2-(Dimethylamino)ethyl methacrylate
DMF Dimethylformamide
E Glutamic Acid
EDC N-Ethyl-N'-(3-dietyhlaminopropyl) carbodiimide
EDT 1,2-ethanedithiol
ELISA Enzyme-linked Immunosorbent Assay
GL Ethyl glycolate methacrylate
hCG human chorionic gonadotropin
IB Isobutyl methacrylate
Me Methyl methacrylate
$NH_2$ 2-Aminoethyl methacrylate hydrochloride
NHS N-bromo succinimide
NHS ester N-succinimidyl ester
PEG Poly(ethylene glycol) methacrylate
RAFT reversible addition fragmentation chain transfer
SAM Self-assembly monolayer
SP 3-Sulfopropyl methacrylate potassium salt
SPR Surface plasmon resonance
TCPS Tissue culture polystyrene
TFA Trifluoroacetic acid
TFE 2,2,2-Trifluoroethyl methacrylate
TM [2-(Methacryloyloxy)ethyl]trimethylammonium chloride
TSTU N,N,N',N'-Tetramethyl-O—(N-succinimidyl)uranium tetrafluoroborate The following examples are provided for the purpose of illustrating, not limiting, the invention.

EXAMPLES

Materials.

Human plasma fibrinogen and chicken egg white lysozyme were purchased from Sigma-Aldrich (Milwaukee, Wis.). Human plasma fibronectin was purchased from Chemicon International (Temecula, Calif.). Human chorionic gonadotropin (hCG) and its monoclonal mouse antibody (mAb; isotype IgG1) were purchased from Scripps Laboratories (San Diego, Calif.). 2-(N,N'-dimethylamino)ethyl methacrylate (DMAEM, 98%), β-propiolactone (95%), copper (1) bromide (99.999%), bromoisobutyryl bromide (98%), 11-mercapto-1-undecanol (97%), 2,2'-bipyridine (BPY 99%), tetrahydrofuran (THF, HPLC grade), NHS, and EDC, were purchased from Sigma-Aldrich (Milwaukee, Wis.). Phosphate-buffered saline (PBS: 0.01 M phosphate, 0.138 M sodium chloride, 0.0027 M potassium chloride, pH 7.4) was purchased from Sigma Chemical Co. Ethanol (absolute 200 proof) was purchased from AAPER Alcohol and Chemical Co. Water used in experiments was purified using a Millipore water purification system with a minimum resistivity of 18.0 MΩ·cm. THF for reactions and washings was dried by sodium before use.

Example 1

Representative Dual-Functional Surface Having Nonfouling Poly(CBMA) Coating

Human plasma fibrinogen and chicken egg white lysozyme were purchased from Sigma-Aldrich (Milwaukee, Wis.). Human plasma fibronectin was purchased from Chemicon International (Temecula, Calif.). Human chorionic gonadotropin (hCG) and its monoclonal mouse antibody (isotype IgG1) were purchased from Scripps Laboratories (San Diego, Calif.). 2-(N,N'-dimethylamino)ethyl methacrylate (DMAEM, 98%), β-propiolactone (95%), copper (I) bromide (99.999%), bromoisobutyryl bromide (98%), 11-mercapto-1-undecanol (97%), 2,2'-bipyridine (BPY 99%) and tetrahydrofuran (THF HPLC grade), N-hydroxysuccinimide (NHS) and 1-ethyl-3-(3-dimethylaminopropyl)-carbodiimide (EDC), were purchased from Sigma-Aldrich (Milwaukee, Wis.). Phosphate buffer saline (PBS, 0.01 M phosphate, 0.138 M sodium chloride, 0.0027 M potassium chloride, pH 7.4) were purchased from Sigma Chemical Co. Ethanol (absolute 200 proof) was purchased from AAPER Alcohol and Chemical Co. Water used in experiments was purified using a Millipore water purification system with a minimum resistivity of 18.0 MΩcm. THF for reactions and washings were dried by sodium before use.

A SPR glass chip was coated with an adhesion-promoting chromium layer (thickness 2 nm) and a surface plasmon active gold layer (48 nm) by electron beam evaporation under vacuum. Before SAM preparation, the substrates were treated as reported method. The initiator, ω-mercaptoundecyl bromoisobutyrate, was synthesized through reaction of bromoisobutyryl bromide and 11-mercapto-1-undecanol using a method published previously.

CBMA was synthesized by reaction of 2-(N,N'-dimethylamino)ethyl methacrylate with β-propiolactone. The ATRP surface initiated polymerization was reported in our previous papers.

Mercaptoundecyl bromoisobutyrate was synthesized through the reaction of bromoisobutyryl bromide and 11-mercapto-1-undecanol using a method published previously. 1H NMR (300 MHz, $CDCl_3$): 4.15 (t, J=6.9 Hz, 2H, $OCH_2$), 2.51 (q, J=7.5 Hz, 2H, $SCH_2$), 1.92 (s, 6H, $CH_3$), 1.57-1.72 (m, 4H, $CH_2$), and 1.24-1.40 (m, 16H, $CH_2$).

CBMA Synthesis.

A carboxybetaine methacrylate (CBMA) monomer, 2-carboxy-N,N-dimethyl-N-(2'-methacryloyloxyethyl)ethanaminium inner salt, was synthesized by reaction of 2-(N,N'-dimethylamino)ethyl methacrylate (DMAEM, 98%) with β-propiolactone (95%). 0.87 g (12 mmol) β-Propiolactone in 10 mL dried acetone was added dropwise to a solution of 1.57 g (10 mmol) DMAEM dissolved in 50 mL dried acetone. The reaction was stirred under nitrogen protection at 15° C. for about 5 hours. The white precipitate was washed with 50 mL dried acetone and 100 mL dried ether. The product was dried under reduced pressure to get CBMA monomer. The monomer was kept at 2-8° C. before the polymerization. Yield: 91%.

Surface Initiated Polymerization on a SPR Sensor.

SPR glass chips were coated with an adhesion-promoting chromium layer (2 nm) and a surface plasmon active gold layer (48 nm) by electron beam evaporation under vacuum. Before SAM preparation, the substrates were washed with pure ethanol, cleaned under UV light, and washed with water and pure ethanol. The initiator SAMs were formed by soaking gold-coated substrates in a pure ethanol solution of 1 mM ω-mercaptoundecyl bromoisobutyrate at room temperature for 24 hours. Before the polymerization, the substrates were rinsed with pure ethanol, followed by THF and dried in a stream of nitrogen.

CuBr and the substrate with immobilized initiators were placed in a reaction tube in a dry box under nitrogen protection. The tube sealed with rubber septum stoppers was taken out. Degassed solution (pure water and methanol in a 1:1 volume ratio) with CBMA and BPY was then transferred to the tube using syringe under nitrogen protection. After the reaction, the substrate was removed and rinsed with ethanol and water, and the samples were kept in water overnight. Rinsing with PBS buffer is also applied to remove unbound polymers before testing. For a typical polymerization, the substrate was reacted with 7.5 mmol CBMA, 2 mmol BPY and 1 mmol CuBr in 25 mL $CH_3OH/H_2O$ (1:1 volume ratio) for 1 hour under nitrogen protection. After a typical ATRP polymerization, homogenous carboxybetaine polymer brushes were grafted on the gold surface of a SPR sensor. The thickness of the polymer layer is around 10-15 nm measured by ellipsometry.

SPR Analysis and Protein Adsorption.

Protein adsorption was measured with a custom-built surface plasmon resonance (SPR) sensor, which is based on wavelength interrogation. A SPR chip (32×18×2 mm) was attached to the base of the prism, and optical contact was established using refractive index matching fluid (Cargille). A four-channel flow cell (contact area: 17×3 mm each) with four independent parallel flow channels was used to contain liquid sample during experiments. A peristaltic pump (Ismatec) was utilized to deliver liquid sample to the four channels of the flow cell. A fibrinogen solution of 1.0 mg/mL in PBS was flowed over the sensor surface at a flow rate of 0.05 mL/min. A SPR detector was used to monitor protein-surface interactions in real time. Wavelength shift was used to measure the change in surface concentration (or mass per unit area).

The smallest change in the signal that can be measured by the SPR sensor was 0.02 nm or lower (i.e., 10 times the standard deviation of baseline noise, which is 0.002 nm for the custom-built SPR sensor used). For normal molecules, at an operating wavelength of around 800 nm, a 1 min SPR wavelength shift corresponds to an adsorption of ~15 ng/cm$^2$ on the surface. For each surface, at least three samples were measured for protein adsorption.

Ellipsometry.

Ellipsometry was performed using a spectroscopic ellipsometer (Sentech SE-850, GmbH). Sample preparation is the same as in XPS experiments. Five separate spots were measured at three different angles of incidence (50, 60 and 70 degrees) in the visible region. The same batch of gold-coated chips was cleaned by UV-ozone cleaner for 20 min, washed with ethanol and Millipore water, and dried with nitrogen. The bare gold-coated chips were used as a reference. The thicknesses of films studied were determined using the Cauchy layer model with an assumed refractive index of 1.45.

Anti-hCG Immobilization on Poly(CBMA)-Grafted SPR Sensors.

The monoclonal mouse anti-hCG was immobilized onto the surface of the polymer brushes by reacting amines of the antibody to the carboxyl groups of the carboxyl groups of the poly(CBMA) using EDC/NHS coupling chemistry. The poly (CBMA)-grafted SPR sensor surface was activated by incubating the SPR chip in a freshly prepared solution containing 2 mg/mL NHS and 2 mg/mL EDC in a mixed solvent of dioxane/water (v/v 14:1) for 1 h at room temperature. The substrate was then removed from the solution, rinsed with 18.2MΩcm DI water, and dried with a flow of nitrogen. The anti-hCG mAb was linked to the activated surface by putting a 10 μL drop of 2 mg/mL anti-hCG in PBS onto the surface, covering the surface with a glass cover slip, and then incubating the mAb with the activated surface for approximately 24 h at 4° C. in a humid environment. The antibody functionalized substrate was washed with 18.2MΩcm DI water and excess activated sites were subsequently blocked by 1 M ethanolamine (pH 8.5) for 10 min remove any unreacted NHS.

Example 2

Optimization of Target Binding Partner Immobilization for a Representative Poly(CBAA) Coated Surface Optimal activation of carboxylates using NHS/EDC method was achieved in situ using water/HCl, pH3.3 as a solvent. Briefly, the polymer surface was activated by injection of freshly prepared solution of NHS (0.05M) and EDC (0.2M) for 10 minutes at temperature of 30° C. Two different antibodies, in particular monoclonal antibody against activated cell leukocyte adhesion molecule (anti-ALCAM) and polyclonal antibody against *Salmonella* (anti-Salm) were immobilized into different spots of the activated poly(CBAA) coated surface under various pH conditions with antibody concentration of 50 ug/mL. The flow rate was 50 ul/min, T=30 C and incubation time was about 15 minutes. After that, the surface was treated with 10 mM PB, 0.75M NaCl, pH 8.8 (PBNa) to remove all non-covalently bound ligands. Effect of pH of running buffer on antibody immobilization is shown in FIG. 7. A typical response to immobilization of antibody at pH 8.0 is shown in FIG. 8. FIG. 9 shows the detection of ALCAM on an anti-ALCAM immobilized surface and a reference surface with immobilized anti-Salm in 50% plasma. CBAA monomer synthesis and poly(CBAA) surface grafting are similar to those for CBMA as described in Example 1 above.

Example 3

Representative Sensors with Dual-Functional Surface Coated with Poly(CBAA) and Activated with TSTU A SPR sensor with a dual-functional surface based on nonfouling poly(CBAA) coating functionalized using the TSTU method was accomplished in this example. A custom-built four-channel spectroscopic surface plasmon resonance sensor was used to monitor poly(CBAA) surface functionalization.

Poly(CBAA) chips were first prepared in the form of Poly (CBAA) esters via ATRP method. The poly(CBAA)-ester surface is then hydrolyzed to achieve zwitterionic nonfouling poly(CBAA) surface. A sensor chip surface with grafted poly (CBAA) esters was washed with MilliQ water, dried with filtered air and mounted into the SPR sensor. The hydrolysis was performed in situ by flowing with 0.1M NaOH, pH 12 for 2 hours along the poly(CBAA) surface. The effectiveness of hydrolysis was checked by injection of highly surface-sticking protein (fibrinogen) with concentration of 1 mg/mL in phosphate buffered saline (PBS), pH 7.4. It was found that 2 hours was sufficient time to fully hydrolyze the poly(CBAA) ester surface.

The zwitterionic poly(CBAA) surface was immersed in solution of TSTU (5 mg/mL) in DMF for 2 hours. After that, the surface was washed with ethanol and dried with filtered air. The chip was immediately mounted into the SPR sensor. The model system of two antibodies was used to demonstrate functionalization of the surface-grafted poly(CBAA). Antibody against activated cell leukocyte adhesion molecule (anti-ALCAM) was immobilized into the measuring channel and antibody against *Salmonella* (anti-Salm) was immobilized into the reference channel. Immobilization was performed in situ in 10 mM sodium acetate buffer, pH 5.0. Antibody concentration was consecutively 10 ug/mL and 50 ug/mL, incubation time was 15 minutes.

FIG. 10 shows sensor response to immobilize ALCAM and *Salmonella* antibodies on the surface of a poly(CBAA) sensor twice (with 10 and 50 ug/ml, respectively) that was activated with TSTU method. FIG. 11 shows the detection of ALCAM using the anti-ALCAM immobilized surface and low background noise (or low non-specific binding) using a non-targeted antigen (i.e., fibrinogen in this case). Residual NHS-esters were transformed back to carboxylate groups by flowing 10 mM phosphate buffer, 150 mM NaCl, pH 8.5 for 5 hours. Fibrinogen with concentration of 1 mg/mL was injected into reference channel to check for the effectiveness of hydrolysis and super nonfouling properties (FIG. 11A). Detection of ALCAM antigen was performed then in PBS buffer. Solution of ALCAM with concentration of 100 ng/mL was injected over the measuring and reference channel for 10 minutes. FIG. 11B shows sensor response to ALCAM binding in the measuring (anti-ALCAM) and reference (anti-Salm) channels. ALCAM antigen was bound specifically to the anti-ALCAM surface. These results suggest that deactivation process was successful and functionalized poly(CBAA) surface kept its super nonfouling properties as well as the biological activity of anti-ALCAM was preserved.

Example 4

Representative Carboxybetaine Hydrogel Preparation

In this example, a poly(CBMA) hydrogel and its resistance to protein adsorption and cell adhesion is described. A CBMA hydrogel was prepared by adding 2.7 M CBMA monomer into tetraethylene glycol dimethacrylate (TEGDMA) (5.9 mol %) and through free radical polymerization initiated by sodium metabisulfite (1.2 mol %) and ammonium persulfate (2.6 mol %) in a mixed solution (ethylene glycol/ethanol/$H_2O$=3:1:1 volume ratio). The reaction was carried out between a pair of glass substrates, separated with a PTFE spacer of 0.4 mm at 37° C. for 12 h. After polymerization, the gel was immersed in a large amount of DI water for three days and water was changed every day to remove residual chemicals. The gel was then equilibrated in sterilized PBS solution, which was changed every day for another two days. Hydrogels were punched into disks with a diameter of 5 mm and stored in sterilized buffer solution before use.

The hydrogel disks were immersed into dioxane of 2 mg/ml NHS and 2 mg/ml EDC in dioxane/water (14:1) mixture for 1 hour at room temperature. The hydrogel disks shrank during the soaking with the dioxane/water solution. The disks were removed from the solution, soaked in Millipore water to swell them back, rinsed with Millipore water, and soaked in PBS buffer for another 30 min. The samples were immersed in a 100 μg/mL fibronectin solution at 4° C. for 24 hours.

Bovine aortic endothelial cells (BAECs) were maintained in continuous growth in Dulbecco's modified Eagle's medium (DMEM), supplemented with 10% fetal bovine serum (FBS), 1% sodium pyruvate, 1% nonessential amino acids, and 2% penicillin streptomycin solution at 37° C. in a humidified atmosphere containing 5% $CO_2$ on tissue culture polystyrene flasks. BAECs were removed from the flask surfaces by washing twice with 10 mL of PBS followed by incubation in 2 mL of trypsin/ethylenediamine tetraacetic acid (0.05%/0.53 mM) for detachment. After cells were detached, cells were then resuspended in 8 mL of DMEM, and the suspension was centrifuged at 1000 rpm for 5 min. The supernatant was removed and the cells were diluted in DMEM with 5% or 10% FBS at a final concentration of $10^5$ cells/mL. The hydrogel disks were washed by PBS in a 24-well plate and 2 mL cell suspension was added to each well. The cells were then incubated with the samples for 3 days at 37° C. in a humidified atmosphere of 5% $CO_2$. The morphology and proliferation of the cells were observed using a Nikon TE200 phase contrast microscope equipped with a digital camera using a 10× objective between 2 hours and 3 days of cultivation. Cell seeding density was determined using a hemocytometer. Cell culture medium and reagents were obtained from Gibco (Gaithersburg, Md.).

Example 5

Representative CBAA-Based Protein Array

Figure 14:
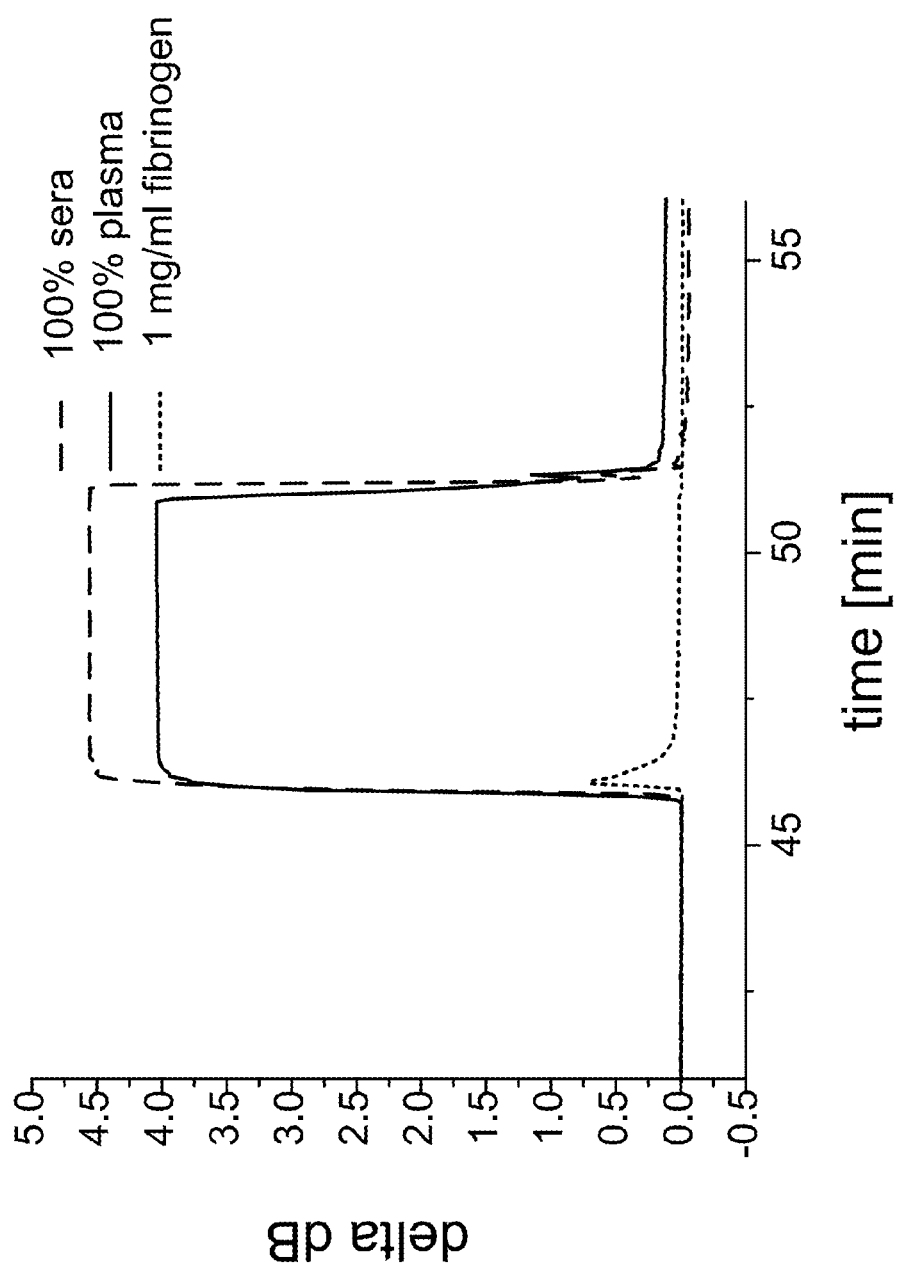
FIG. 14 compares SPR sensorgrams for a representative CBAA polymer surface of the invention useful for protein assays showing superlow fouling of the surface to complex media including 100% serum, 100% plasma, and 1 mg/ml fibrinogen.

Protein microarrays on polyCBAA surfaces were made using a microcontact printing robot (Spotbot, Telechem Inc.) to monitor specific protein binding events using a surface plasmon resonance (SPR) imaging sensor with polarization contrast. The array is illustrated schematically in FIG. 13A. The SPR imaging sensor is based on intensity modulation, which allows measurements of spatially resolved real-time changes of SPR signals. FIG. 14 shows three sensorgrams corresponding to protein adsorption from three complex matrices (100% sera, 100% plasma, and 1 mg/ml fibrinogen), each flowed for five minutes at 30 microliters per minute on the CBAA surface. In the sensorgrams, the first five minutes is a baseline established by flowing phosphate buffered saline (PBS) pH 7.4, followed by the addition of each of the complex media. The complex media have a different RI causing a significant shift in the SPR. After five minutes the solution is changed back to PBS, so that the background refractive index is now identical to that during the collection of the original baseline. Any shift in the baseline before and after the addition of the complex media represents a quantitative measurement proteins bound to the surface. From FIG. 14 there was no measurable binding from 100% plasma or 1 mg/ml fibrinogen, while the 100% serum has minimal binding.

Figure 15:
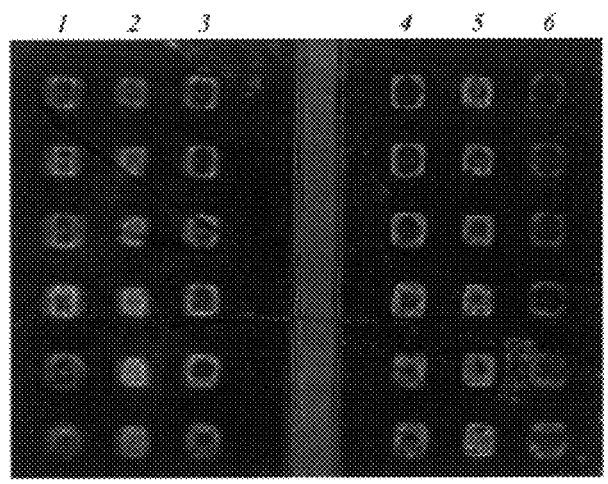
FIG. 15 is a spatially-resolved image of a representative protein microarray of the invention from surface plasmon resonance (SPR) imaging, intensity changes from dark to bright represent protein binding on the surface, anti-hCG and anti-salmonella proteins were printed in 500 μm spots using a microcontact printing robot, column 1, 3, 4, and 6 are anti-hCG and column 2 and 5 are anti-Salmonella.
Figure 16:
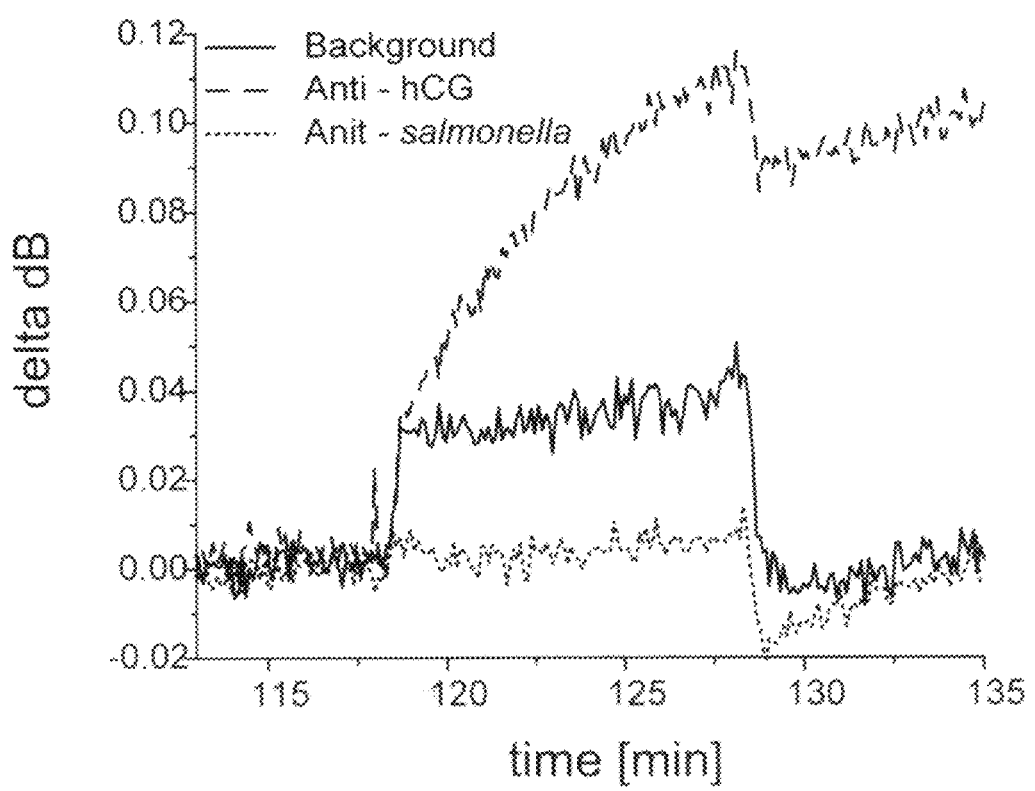
FIG. 16 compares SPR sensorgrams for a representative CBAA polymer surface of the invention useful for specific detection of 10 mg/mL hCG on an anti-hCG protein spot, no detection is observed on the reference anti-Salmonella protein spot or the background.

The CBAA surface was specifically functionalized with two antibodies in a microarray pattern. FIG. 15 shows the SPR image of the antibodies on the surface. The difference in the brightness of the background and the protein spots quantitatively represents the amount of proteins immobilized. The protein microarray was produced by first activating the CBAA surface by reacting it with a solution containing 0.1M EDC and 0.05 M NHS in 100 mM sodium acetate buffer at pH 3.3 for 30 minutes. Using a microcontact printing robot equipped with 500 μm diameter stealth pins, the anti-human chorionic gonadotropin (hCG) and anti-Salmonella antibodies with printed onto the activated polymer surface and allowed to react for 30 minutes. Excess protein was then rinsed from the surface and activated background was deactivated by soaking the microarray chip in a solution of 100 mM hydroxylamine in 100 mM sodium carbonate buffer at pH 9.0 for about 18 hours, in order to hydrolyze the active NHS esters back to carboxylic acids returning the surface to its zwitterionic state with inherent non-fouling characteristics. FIG. 16 shows the specific detection of 10 μg/ml hCG on the spots with anti-hCG while no detection is observed on the reference anti-Salmonella spot or the background. The CBAA surface not only has a nonfouling background, but also can be specifically functionalized with protein enabling detection of protein-protein binding events. The surface chemistry has wide range of application, especially in biomedical diagnostics, where detections are commonly performed in complex biological media like blood. Many new label-free methods such as SPR have become popular, however without non-fouling background and specific surface, deconvolution of specific and non-specific binding is difficult.

While illustrative embodiments have been illustrated and described, it will be appreciated that various changes can be made therein without departing from the spirit and scope of the invention.

The embodiments of the invention in which an exclusive property or privilege is claimed are defined as follows:

1. A substrate having a modified surface, comprising,
    (a) a polymer attached to a surface of a substrate, wherein the polymer comprises a plurality of carboxylic acid groups and a plurality of positive charged groups, and wherein the polymer is substantially electronically neutral; and
    (b) a target binding partner, covalently coupled to the polymer, and wherein the target binding partner has affinity toward a target molecule.

2. The substrate of claim 1, wherein the polymer is covalently coupled to the surface.

3. The substrate of claim 1, wherein the polymer is covalently coupled to the surface through a monolayer comprising alkylene moieties.

4. The substrate of claim 1, wherein the polymer has the formula:

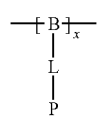

wherein B is selected from the group consisting of

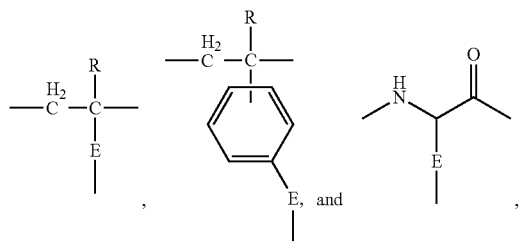

wherein R is selected from the group consisting of hydrogen and substituted or unsubstituted alkyl; and E is selected from the group consisting of substituted or unsubstituted alkylene, —(CH$_2$)$_p$C(O)O—, and —(CH$_2$)$_p$C(O)NR$^2$—, wherein p is an integer from 0 to 12, and R$^2$ is selected from the group consisting of hydrogen and substituted or unsubstituted alkyl;

L is a straight or branched alkylene group optionally including one or more oxygen atoms;

P is selected from the group consisting of

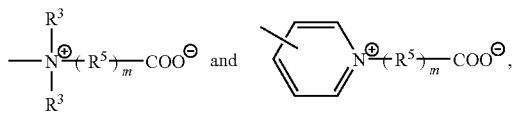

wherein R$^3$ and R$^4$ are independently selected from the group consisting of hydrogen and substituted or unsubstituted alkyl group, R$^5$ is selected from the group consisting of substituted or unsubstituted alkylene, phenylene, and polyether groups, and m is an integer from 1 to 7; and x is an integer from 3 to 1000.

5. The substrate of claim 1, wherein the polymer has the formula:

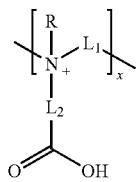

wherein R is selected from the group consisting of hydrogen and substituted or unsubstituted alkyl;

L$_1$ and L$_2$ are independently a straight or branched alkylene group optionally including one or more oxygen atoms; and x is an integer from 3 to 1000.

6. The substrate of claim 1, wherein the polymer has the formula:

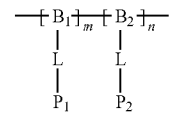

wherein B$_1$ and B$_2$ are independently selected from the group consisting of

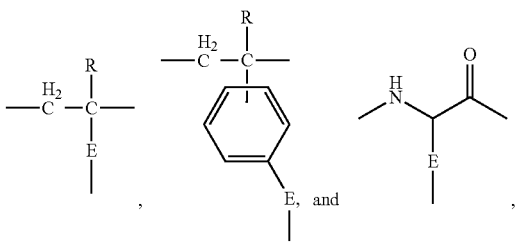

wherein R is selected from the group consisting of hydrogen and substituted or unsubstituted alkyl; and E is selected from the group consisting of substituted or unsubstituted alkylene, —(CH$_2$)$_p$C(O)O—, and —(CH$_2$)$_p$C(O)NR$^2$—, wherein p is an integer from 0 to 12, and R$^2$ is selected from the group consisting of hydrogen and substituted or unsubstituted alkyl;

L is a straight or branched alkylene group optionally including one or more oxygen atoms;

P$_1$ is a positively charged group;

P$_2$ is carboxylic acid group;

m is an integer from 3 to 1000; and n is an integer from 3 to 1000.

7. The substrate of claim 6, wherein P$_1$ is nitrogen in an aromatic ring or NR$_5$R$_6$, wherein R$_5$ and R$_6$ are independently substituted or unsubstituted alkyl group.

8. The substrate of claim 1, wherein the polymer is a poly(carboxybetaine).

9. The substrate of claim 1, wherein the target binding partner is selected from the group consisting of enzymes, antibodies, antigens, receptors, and ligands.

10. The substrate of claim 1, wherein the target binding partner is selected from the group consisting of proteins, peptides, nucleic acids, and sugars.

11. A substrate having a modified surface, comprising,
(a) a polymer coating attached to a surface of a substrate, wherein the polymer coating comprises a polymer having a plurality of carboxylic acid groups and a plurality of positive charged groups, and wherein the polymer coating is substantially electronically neutral; and
(b) a target binding partner covalently coupled to the polymer coating, and wherein the target binding partner has affinity toward a target molecule.

12. The substrate of claim 11, wherein the polymer coating is covalently coupled to the surface.

13. The substrate of claim 11, wherein the polymer coating is covalently coupled to the surface through a monolayer comprising alkylene moieties.

14. The substrate of claim 11, wherein the polymer has the formula:

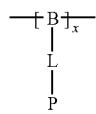

wherein B is selected from the group consisting of

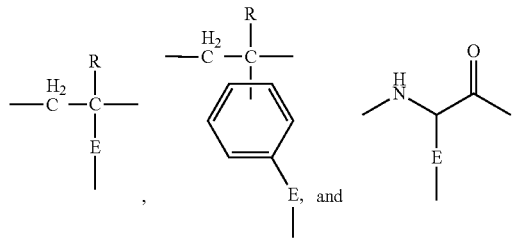

wherein R is selected from the group consisting of hydrogen and substituted or unsubstituted alkyl; and E is selected from the group consisting of substituted or unsubstituted alkylene, —(CH$_2$)$_p$C(O)O—, and —(CH$_2$)$_p$C(O)NR$^2$—, wherein p is an integer from 0 to 12, and R$^2$ is selected from the group consisting of hydrogen and substituted or unsubstituted alkyl;

L is a straight or branched alkylene group optionally including one or more oxygen atoms;

P is selected from the group consisting of

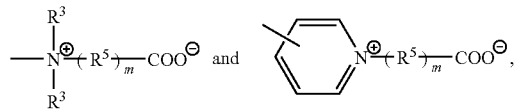

wherein R$^3$ and R$^4$ are independently selected from the group consisting of hydrogen and substituted or unsubstituted alkyl group, R$^5$ is selected from the group consisting of substituted or unsubstituted alkylene, phenylene, and polyether groups, and m is an integer from 1 to 7; and x is an integer from 3 to 1000.

15. The substrate of claim 11, wherein the polymer has the formula:

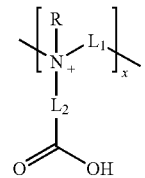

wherein R is selected from the group consisting of hydrogen and substituted or unsubstituted alkyl;

L$_1$ and L$_2$ are independently a straight or branched alkylene group optionally including one or more oxygen atoms; and x is an integer from 3 to 1000.

16. The substrate of claim 11, wherein the polymer has the formula:

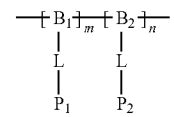

wherein B$_1$ and B$_2$ are independently selected from the group consisting of

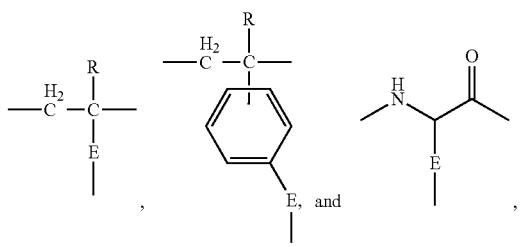

wherein R is selected from the group consisting of hydrogen and substituted or unsubstituted alkyl; and E is selected from the group consisting of substituted or unsubstituted alkylene, —(CH$_2$)$_p$C(O)O—, and —(CH$_2$)$_p$C(O)NR$^2$—, wherein p is an integer from 0 to 12, and R$^2$ is selected from the group consisting of hydrogen and substituted or unsubstituted alkyl;

L is a straight or branched alkylene group optionally including one or more oxygen atoms;

P$_1$ is a positively charged group;

P$_2$ is carboxylic acid group;

m is an integer from 3 to 1000; and n is an integer from 3 to 1000.

17. The substrate of claim 16, wherein $P_1$ is nitrogen in an aromatic ring or $NR_5R_6$, wherein $R_5$ and $R_6$ are independently substituted or unsubstituted alkyl group.

18. The substrate of claim 11, wherein the polymer coating is a polymer brush.

19. The substrate of claim 11, wherein the polymer is a poly(carboxybetaine).

20. The substrate of claim 11, wherein the target binding partner is selected from the group consisting of enzymes, antibodies, antigens, receptors, and ligands.

21. The substrate of claim 11, wherein the target binding partner is selected from the group consisting of proteins, peptides, nucleic acids, and sugars.

* * * * *